US011238992B2

(12) United States Patent
Aronson

(10) Patent No.: US 11,238,992 B2
(45) Date of Patent: *Feb. 1, 2022

(54) CONFIGURABLE CONCISE DATASETS PLATFORM

(71) Applicant: Jeffry David Aronson, Austin, TX (US)

(72) Inventor: Jeffry David Aronson, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/165,191

(22) Filed: Feb. 2, 2021

(65) Prior Publication Data

US 2021/0158972 A1 May 27, 2021

Related U.S. Application Data

(63) Continuation-in-part of application No. 16/891,080, filed on Jun. 3, 2020, now Pat. No. 10,943,693, which
(Continued)

(51) Int. Cl.
*G16H 50/70* (2018.01)
*G06F 16/2455* (2019.01)
(Continued)

(52) U.S. Cl.
CPC .......... *G16H 50/70* (2018.01); *A61B 5/0823* (2013.01); *A61B 5/1101* (2013.01);
(Continued)

(58) Field of Classification Search
CPC ........ G16H 50/70; G16H 40/67; G16H 10/60; G16H 15/00; G16H 50/20; G16H 70/20;
(Continued)

(56) References Cited

U.S. PATENT DOCUMENTS

2009/0067686 A1* 3/2009 Boshra ............... G07C 9/37 382/124
2011/0040574 A1* 2/2011 Fung ............... G06Q 30/0239 705/2
(Continued)

OTHER PUBLICATIONS

Schiavone et al., Continuous Authentication and Non-repudiation for the Security of Critical Systems, Sep. 2016, IEEE 35th Symposium on Reliable Distributed Systems, pp. 207-208 (Year: 2016).*

*Primary Examiner* — Kenneth W Chang
(74) *Attorney, Agent, or Firm* — John A. Fortkort; Fortkort & Houston PC

(57) ABSTRACT

A scalable configurable universal complete spectrum concise datasets platform is provided that utilizes measure points from sensor-observation-derived representations or concise datasets in the making of selected cyber determinations regarding or utilizing sensor observations or sensor observation subjects. The platform utilizes necessary resources and predetermined criteria in the making of selected cyber determinations, the platform utilizes measure points and personalized processes in the accurate or reliable locating of selected analytically rich aspects, characteristics or features from sensor-observation-derived representations, wherein appropriate informational representations are assigned to selected analytically rich aspects, characteristics, features, measure points or the sensor observation and stored in concise datasets where they may be utilized in real-time or thereafter in the making of selected cyber determinations regarding or utilizing sensor observations or sensor observation subjects. The platform is configurable for being utilized as a touchless user interface, a 100% accurate cyberspace identity test or a universal health metrics monitor.

26 Claims, 1 Drawing Sheet

Related U.S. Application Data is a continuation-in-part of application No. 15/981,785, filed on May 16, 2018, now Pat. No. 10,943,097.

(60) Provisional application No. 62/507,128, filed on May 16, 2017.

(51) Int. Cl.

| | | |
|---|---|---|
| *G16H 40/67* | (2018.01) | |
| *G16H 70/20* | (2018.01) | |
| *G16H 15/00* | (2018.01) | |
| *G16H 50/20* | (2018.01) | |
| *G16H 10/60* | (2018.01) | |
| *G06Q 50/26* | (2012.01) | |
| *G16H 40/20* | (2018.01) | |
| *A61B 5/1172* | (2016.01) | |
| *A61B 5/1171* | (2016.01) | |
| *A61B 5/08* | (2006.01) | |
| *A61B 5/11* | (2006.01) | |
| *A61B 5/00* | (2006.01) | |
| *G06F 16/23* | (2019.01) | |
| *G06F 3/01* | (2006.01) | |
| *G06K 9/00* | (2006.01) | |

(52) U.S. Cl.
CPC .......... *A61B 5/1172* (2013.01); *A61B 5/1176* (2013.01); *A61B 5/4222* (2013.01); *A61B 5/4803* (2013.01); *G06F 16/2379* (2019.01); *G06F 16/24558* (2019.01); *G06Q 50/265* (2013.01); *G16H 10/60* (2018.01); *G16H 15/00* (2018.01); *G16H 40/20* (2018.01); *G16H 40/67* (2018.01); *G16H 50/20* (2018.01); *G16H 70/20* (2018.01); *G06F 3/011* (2013.01); *G06K 9/00067* (2013.01); *G06K 9/00268* (2013.01); *G06K 9/00362* (2013.01)

(58) Field of Classification Search
CPC .......... G06F 16/24558; G06F 16/2379; A61B 5/0823; A61B 5/1101; A61B 5/1172; A61B 5/1176; A61B 5/4222; A61B 5/4803

See application file for complete search history.

(56) References Cited

U.S. PATENT DOCUMENTS

| | | | |
|---|---|---|---|
| 2011/0282168 A1* | 11/2011 | Weiss | G16H 40/67 600/323 |
| 2012/0096549 A1* | 4/2012 | Amini | H04L 63/1433 726/23 |
| 2013/0057385 A1* | 3/2013 | Murakami | G05B 19/00 340/5.82 |
| 2016/0051169 A1* | 2/2016 | Hong | A61B 5/7405 600/595 |

* cited by examiner

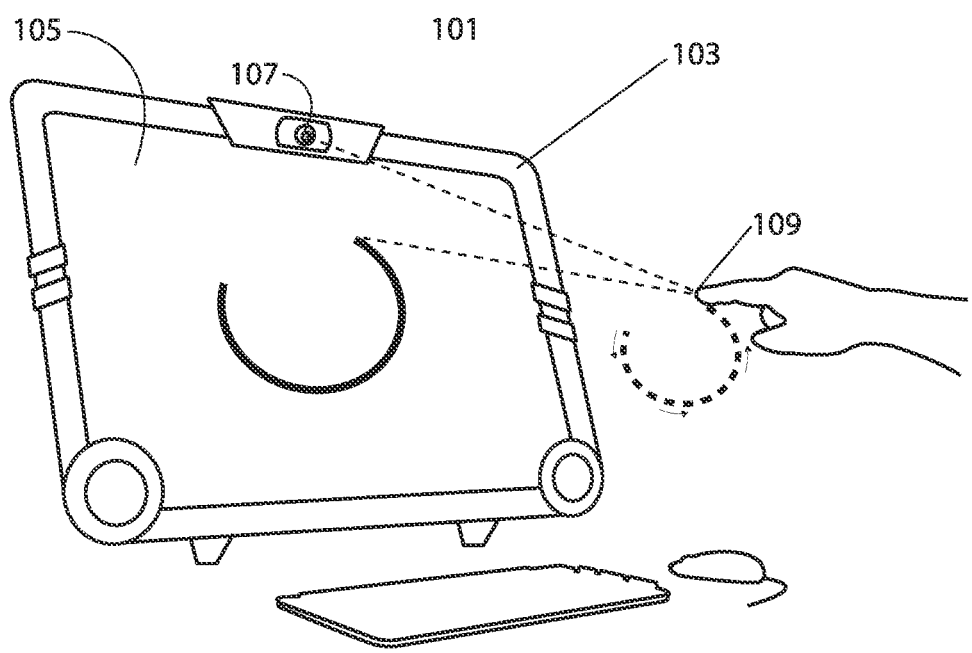

CONFIGURABLE CONCISE DATASETS PLATFORM

CROSS-REFERENCE TO RELATED APPLICATIONS

This application is a continuation-in-part application of U.S. patent application Ser. No. 16/891,080, filed Jun. 3, 2020, entitled "Concise Datasets Platform", having the same inventor, now allowed, which is incorporated herein by reference in its entirety; which application is a continuation-in-part application of U.S. patent application Ser. No. 15/981,785, filed May 16, 2018, entitled "Scalable Configurable Universal Full Spectrum Cyber Process That Utilizes Measure Points From Sensor Observation-Derived Representations or Analytically Rich Sparse Data Sets For Making Cyber Determinations Regarding or Utilizing Sensor Observations or Sensor Observation Subjects", having the same inventor, now allowed, which is incorporated herein by reference in its entirety; which application claims the benefit of priority from U.S. provisional application No. 62/507,128, entitled "Scalable Universal Full Spectrum Cyber Determining Process That May Utilize Reference Points Located On Sensor-Observation-Derived Representations", having the same inventor, which was filed May 17, 2017, and which is incorporated herein by reference in its entirety.

FIELD OF THE DISCLOSURE

The present disclosure relates generally to a platform of cyber processes, procedures and devices that utilize measure points or concise datasets in the making of selected cyber determinations regarding or utilizing sensor observations or sensor observation subjects, and more particularly to a scalable configurable universal full spectrum concise datasets platform that is configurable for selecting, deriving or utilizing concise datasets or measure points in its making of selected cyber determinations regarding or utilizing sensor observations or sensor observation subjects.

BACKGROUND OF THE DISCLOSURE

Prior art processes for making cyber determinations regarding or utilizing sensor observations or sensor observation subjects cannot answer the world's ever-increasing needs for interoperable processes or procedures that quickly, efficiently, accurately or reliably make any cyber determination from a spectrum of cyber determinations regarding or utilizing sensor observations or sensor observation subjects.

A few examples of needs for cyber determinations regarding or utilizing sensor observations or sensor observation subjects that are not being met by prior art include: (a) constantly making accurate or reliable real-time cyber determinations regarding any one specific person's identity, (b) the making of the spectrum of real-time cyber determinations that are needed for autonomous operations of vehicles or other devices, (c) the making of accurate or reliable cyber determinations that are medical diagnoses or that are used in the making of medical diagnoses, (d) the making of real-time cyber determinations that any one specific person has an imminent intent to do harm, (e) the making of real-time cyber determinations regarding precisely what a person is looking at, or (f) the making of cyber determinations regarding the state of a specific person's mental or physical health.

SUMMARY OF THE DISCLOSURE

Unless otherwise specified herein, throughout this entire disclosure, use of the singular form of any word, phrase or statement indicates either the singular or the plural form of the word, phrase or statement, and use of the plural form of any word, phrase or statement indicates either the singular or the plural form of the word, phrase or statement. Additionally, the term "or" shall be construed as the logically inclusive "or". Hence, the statement "A or B" shall be true if: (a) only A is true, (b) only B is true, or (c) both A and B are true; the notation "A and/or B" explicitly refers to the logically inclusive "or".

Prior art processes or procedures do not answer current needs for the simple, efficient, accurate or reliable making of selected cyber determinations regarding or utilizing sensor observations or sensor observation subjects.

Further, prior art processes or procedures do not answer current needs for cyber processes or procedures that are utilizable in the making of a spectrum of cyber determinations regarding or utilizing a spectrum of sensor observations or a spectrum of sensor observation subjects.

The disclosed scalable configurable universal full spectrum concise datasets platform is configurable for utilizing informational representations from sensor observations in the answering of selected questions (the making of selected cyber determinations) regarding or utilizing sensor observations or sensor observation subjects.

The platform is configurable for utilizing measure points in the locating of selected analytically rich aspects, characteristics or features from sensor-observation-derived representations of sensor observations or sensor observation subjects.

Once the questions to be answered by the platform have been selected, then determinations are made regarding which analytically rich aspects, characteristics or features from sensor-observation-derived representations will be used for accurately or reliably answering or aiding in the answering of the selected questions.

The platform is configurable for answering selected questions regarding or utilizing sensor observations or sensor observation subjects through utilization of: (a) information, (b) informational representations from sensor observations, or (c) informational representations that were derived from the processing of information or informational representations from sensor observations.

Using a video camera that is permanently installed or configured to observe the face of the driver of a vehicle as an example, the platform is configurable for answering one question regarding one sensor observation subject. In the case of this example, the question is: Has the driver of the vehicle fallen asleep?

The platform is configurable for utilizing only two measure points that are located on sensor-observation-derived representations of a vehicle driver's face for continuously answering the above question as concisely or efficiently as possible. One measure point locates the image sensor-observation-derived representation of the bottom center of the left upper eyelid and the second measure point locates the image sensor-observation-derived representation of the top center of the lower eyelid of the same eye.

The platform is configurable for assigning appropriate standard informational representations regarding or utilizing each of the two selected measure points. Wherein, the platform is further configurable for selecting the X (horizontal) or Y (vertical) line locations where each measure point will be located on a sensor-observation-derived representation's pixel grid. The distance between the two measure points, if any, is used to determine if the person's eyelids are closed during any number of sequential video images.

Should the horizontal lines that both of the measure points were located on drop down together for at least a specified number of lines over a specified number of sequential video images, then the informational representations regarding changes in the horizontal line location is utilizable in the making of a selected cyber determination that the driver's head has dropped a specific distance and at a specific rate of drop. Informational representations regarding the distance and rate of drop of the driver's head along with informational representations regarding the duration of time that the driver's eyelids have been closed can be used in the making of the cyber determination that the driver of the vehicle has fallen asleep.

The concise dataset from the previous example includes informational representations regarding only two pixels from the over two million pixels of each 1080p video-formatted image. Informational representations regarding the two pixels can easily be used in the answering of the selected question: has the driver of the vehicle fallen asleep? This is a simple question that prior art is not able to efficiently or reliably answer due, at least in part, to prior art's use of the far more complex processes or procedures in its attempt to accurately or reliably answer the question. Further, utilization of the platform reduces the original image sensor observation dataset regarding over two million pixels per image to a simple or efficient working concise dataset that is comprised of informational representations regarding the X and Y line locations of only two pixels per image. This results in a one million-to-one reduction in the size of the working dataset that is used by the platform in the answering of the selected question. Further, since the selected question is accurately or reliably answered using data regarding only two pixels per sequential video image, then the remainder of the pixels that are used by prior art could be considered to be confusing or unnecessary noise.

The platform is configurable for employing any process or procedure from a spectrum of processes or procedures that are utilizable in the making of selected cyber determinations regarding or utilizing what has been observed where a measure point has been located upon a sensor-observation-derived representation. In the case of this example, the platform is configurable for utilizing a concise dataset regarding only the two eyelid-representation-located measure points, wherein the platform utilizes only the X and Y line locations of the two measure points per image in the making of the selected cyber determination.

Concise datasets include selected sensor data or derived data. Using video-formatted image sensor observations as an example, selected sensor data only includes selected data in their original sensor observation dataset's data format. The informational representations from original sensor observation data are typically regarding the X and Y line locations of each pixel on a sensor-observation-derived representation's pixel grid and the measured levels of red, green or blue light that were observed at each pixel from a sensor-observation-derived representation.

The derived data from concise datasets includes data that were derived from the processing of selected sensor data or other derived data.

As an example, the platform utilizes one measure point in the locating of a pulse point on a sensor-observation-derived representation of a specific person's face. A scalable configurable grid (explained later in this disclosure) is utilized for structuring a twenty-one by twenty-one-pixel square with the measure point at its center. The sums of the measurements of observed levels of red, blue or green light from each column or each row of pixels from within the scalable configurable grid are stored as derived data where they may then be utilized in the making of a selected cyber determination that a heartbeat has occurred.

In addition, the platform is configurable for utilizing the sums from one or more columns or rows from the scalable configurable grid in the making of cyber determinations regarding the person's blood pressure.

Data from selected sensor data or selected derived data are stored for utilization in the making of one or more selected cyber determinations-cyber determinations that may be made in real time or at any time thereafter. The platform is configurable for having no further use for a sensor observation dataset when the processing of all selected derived data has been finished and the selected sensor data or derived are included in concise datasets. At this point in the operations of the platform, the original sensor observation datasets may be deleted or stored for later use.

The platform is configurable for comparing informational representations from first series observations of known analytically rich aspects, characteristics or features of or from sensor observations or sensor observation subjects to informational representations from second series observations of yet-to-be-determined analytically rich aspects, characteristics or features of or from sensor observations or sensor observation subjects.

To accurately or reliably utilize informational representations from concise datasets in the making of selected cyber determinations, the processing of the first series observations and the processing of the second series observations of the same subject should result in the platform's assignment of the same standard informational representations to both sensor observations. The platform is configurable for utilizing the same standard processes or procedures in the processing of second series observations that were used in the processing of the first series observations to which they will be compared. Further, the platform is configurable for utilizing the same processes or procedures for all operations of the processing of second series observations as were used for the processing of the first series observations that the second series observations will be compared to.

Incorporating use of a working dataset regarding only the two eyelid representation located measure points is an example of the platform's utilization of a best performing blend of as simple, concise and efficient processes or procedures as possible.

The platform, through utilization of measure points or concise datasets, is configurable for accurately or reliably making any cyber determinations selected from a spectrum of cyber determinations regarding or utilizing sensor observations or sensor observation subjects and the platform may be configured to do so utilizing combinations of processes or procedures that enable operations of the platform to be as simple, concise and efficient as possible.

The present disclosure pertains to a scalable configurable universal complete spectrum concise datasets platform of processes, procedures, methods, formulas, sensors and computing devices, wherein the concise datasets platform selects, derives or utilizes data for or from concise datasets;

wherein, the concise datasets are utilizable in the making of at least one selected cyber determination regarding or utilizing at least one sensor observation or at least one sensor observation subject, the concise datasets platform is comprised of:

a set of resources that include (a) at least one computing device, (b) at least one sensor, (c) selected necessary programming, (d) selected information, (e) criteria selected from a spectrum of criteria that may be utilized by the platform, and (f) other necessary resources; wherein the at least one utilized computing device includes at least one tangible, non-transient memory device and at least one input device or at least one output device;

wherein the concise datasets platform utilizes all or part of the set of resources for (i) the selecting or deriving of data that is to be included in at least one concise dataset, or (ii) the making of at least one selected cyber determination regarding or utilizing at least one sensor observation or at least one sensor observation subject;

wherein the at least one concise dataset is utilizable in the making of at least one selected cyber determination regarding or utilizing the at least one sensor observation or the at least one sensor observation subject;

wherein the at least one concise dataset is comprised of selected sensor data or selected derived data;

wherein the selected sensor data is comprised of at least one informational representation that was selected from at least one sensor observation dataset;

wherein the derived data is comprised of at least one informational representation that was derived from the processing of at least one informational representation that was selected from at least one sensor observation dataset or the processing of at least one informational representation that was selected from derived data;

wherein processes, procedures, methods or formulas that are utilized in the processing of the derived data are selected from a spectrum of processes, procedures, methods or formulas that may be utilized in the deriving of data for or from concise datasets;

wherein data from the selected sensor data or the selected derived data are utilizable by the platform in the making of the at least one selected cyber determination regarding or utilizing the at least one sensor observation or the at least one sensor observation subject;

wherein the concise datasets platform is configurable for utilizing at least one measure point in the locating of at least one selected analytically rich aspect, characteristic or feature of or from at least one sensor-observation-derived representation of at least one sensor observation or at least one sensor observation subject;

wherein the at least one measure point is utilizable by the platform in the making of the at least one selected cyber determination regarding or utilizing sensor observations or sensor observation subjects;

wherein the at least one analytically rich aspect, characteristic or feature of or from the at least one sensor-observation-derived representation that is located through utilization of the at least one measure point, and the at least one measure point are each assigned at least one appropriate informational representation;

wherein the at least one analytically rich aspect, characteristic or feature of or from the at least one sensor observation or the at least one sensor observation subject are selected from a spectrum of analytically rich aspects, characteristics or features of or from sensor observations or sensor observation subjects;

wherein the at least one analytically rich aspect, characteristic or feature of or from the at least one measure point is selected from a spectrum of analytically rich aspects, characteristics or features of or from measure points;

wherein the at least one cyber determination is selected from a spectrum of cyber determinations that may be made regarding or utilizing sensor observations, sensor observation subjects or measure points;

wherein the spectrum of cyber determinations that may be made regarding or utilizing sensor observations, sensor observation subjects or measure points includes at least one cyber determination that identifies at least one tell that is utilizable in the accurate or reliable making of at least one selected cyber determination regarding or utilizing sensor observations, sensor observation subjects or measure points;

wherein the at least one tell is from a spectrum of sensor-observable tells regarding or utilizing sensor observations, sensor observation subjects or measure points;

wherein the at least one selected cyber determination is utilizable for at least one purpose selected from a spectrum of purposes for which cyber determinations regarding or utilizing sensor observations, sensor observation subjects or measure points may be utilized;

wherein the concise datasets platform is configurable for making the at least one selected cyber determination in real time, or at one or more times thereafter;

wherein the concise datasets platform is configurable for making at least one member selected from the group consisting of (a) one-time single cyber determinations regarding or utilizing sensor observations, sensor observation subjects or measure points, (b) intermittently provided cyber determinations regarding or utilizing sensor observations, sensor observation subjects or measure points, or (c) constantly provided cyber determinations regarding or utilizing sensor observations, sensor observation subjects or measure points;

wherein the selected information is from a spectrum of information that may be utilized by the concise datasets platform in the making of the selected cyber determinations;

wherein the spectrum of information includes information from at least one sensor observations;

wherein the selected information is from one or more points in time, or from one or more periods of time;

wherein the at least one sensor observation is made by at least one sensor selected from a spectrum of sensors that are utilized in the making of selected cyber determinations regarding or utilizing sensor observations or sensor observation subjects;

wherein the concise datasets platform is configurable and all or part of its resource may be configured for utilization in at least one configuration;

wherein the concise datasets platform is scalable in regard to included or utilized concise datasets platform resources to fall at any one point in a range of from a minimum to a maximum, wherein at the minimum the platform is scaled to include or utilize only the resources that are needed in the making of the least complex selected cyber determination, in regard to included or utilized platform resources, and wherein at the maximum the platform is scaled to include or utilize all platform resources;

wherein the at least one sensor observation or the at least one sensor observation subject are selected from a spectrum of sensor observations or sensor observation subjects; and wherein the concise datasets platform further comprises utilizing, in any sequence, at least one part of at least one operation selected from the group consisting of (a) first series observation operations, wherein the concise datasets platform is configured for utilizing at least one first series sensor observation, wherein at least one first series sensor observation or at least one subject of the at least one first series sensor observation has at least one previously determined analytically rich aspect, characteristic or feature, the concise datasets platform recognizes the at least one previously determined aspect, characteristic or feature, the concise datasets platform assigns at least one appropriate informational representation regarding the at least one recognized aspect, characteristic or feature of or from the at least one sensor observation or the at least one sensor observation subject, the at least one assigned informational representation is utilizable by the concise datasets platform in the making of at least one selected cyber determination regarding or utilizing the at least one sensor observation or the at least one sensor observation subject, the concise datasets platform includes at least one assigned informational representation of or from the at least one first series observation in at least one first series observation concise dataset, (b) second series observation operations, wherein the concise datasets platform is configured for utilizing at least one second series sensor observation, wherein at least one second series sensor observation or at least one subject of the at least one second series observation has at least one selected yet-to-be-determined analytically rich aspect, characteristic or feature, the concise datasets platform recognizes the at least one yet-to-be-determined analytically rich aspect, characteristic or feature, the concise datasets platform assigns at least one appropriate informational representation regarding the at least one yet-to-be-determined analytically rich aspect, characteristic or feature of or from the at least one sensor observation or the at least one sensor observation subject, the at least one assigned informational representation is utilizable by the concise datasets platform in the making of at least one selected cyber determination regarding or utilizing the sensor observations or sensor observation subjects, the concise datasets platform includes at least one assigned informational representation of or from the at least one second series observation in at least one second series observation concise dataset, (c) measure point operations, wherein the concise datasets platform utilizes at least one measure point in the locating of at least one selected analytically rich aspect, characteristic or feature of or from at least one sensor-observation-derived representation of at least one sensor observation or at least one sensor observation subject, wherein the concise datasets platform assigns at least one appropriate informational representation regarding the at least one measure point or the at least one selected analytically rich aspect, characteristic or feature, wherein the at least one informational representation is stored or utilized in the making of at least one selected cyber determination regarding or utilizing at least one sensor observation or at least one sensor observation subject, (d) concise datasets operations, wherein the concise datasets platform selects, derives or utilizes data for or from concise datasets, wherein the concise datasets are comprised of selected sensor data or selected derived data, wherein the selected sensor data is comprised of at least one informational representation that was selected from the informational representations of at least one sensor observation dataset, and wherein the selected derived data is comprised of at least one informational representation that was derived from (i) the processing of at least one selected informational representation from the at least one sensor observation dataset, or (ii) the processing of at least one selected informational representation from the derived data, wherein at least one informational representation that was derived from the processing of the at least one selected sensor observation dataset or from the derived data is utilizable by the concise datasets platform in the making of at least one selected cyber determination regarding or utilizing at least one sensor observation or at least one sensor observation subject, (e) matching operations, wherein the concise datasets platform matches at least one selected informational representation from at least one second series observation with at least one selected comparable informational representation from at least one first series observation concise dataset, (f) comparing operations, wherein the concise datasets platform compares at least one selected informational representation from at least one second series observation concise dataset with at least one selected informational representation from at least one first series observation concise dataset, wherein the platform utilizes the comparison for: (i) providing at least one conclusion, or (ii) making at least one selected cyber determination, (g) determining operations, wherein the concise datasets platform utilizes the at least one conclusion from the at least one comparing operation, or the selected information, in the making of the at least one selected cyber determination regarding or utilizing at least one sensor observation or at least one sensor observation subject, and (h) reporting operations, wherein the concise datasets platform makes at least one selected report regarding or utilizing at least one aspect, characteristic or feature of or from the operations of the concise datasets platform.

The platform is further configurable for (a) at least one person, (b) at least one process, (c) at least one procedure, or (d) any combination thereof to be utilized in the selecting of at least one selected aspect, characteristic or feature of or from at least one operation of the concise datasets platform, wherein the at least one process or the at least one procedure are selected from a spectrum of processes or procedures that may be utilized in the selecting of the at least one aspect, characteristic or feature of or from at least one operation of the concise datasets platform.

The platform is further configurable for utilizing at least one member selected from the group consisting of (a) processes, (b) procedures, (c) data, (d) information, (e) interactions by at least one person, or (f) any combination thereof, in the making of at least one selected determination regarding the point or points where at least one selected measure point will be located on at least one sensor-observation-derived representation, and wherein the at least one selected measure point is utilizable in the making of at least one type of cyber determination selected from the group consisting of:

(a) cyber determinations of the point or points where at least one selected measure point will be located on at least one sensor-observation-derived representation of only one specific sensor observation subject, (b) cyber determinations of the point or points where at least one selected measure point will be located on at least one sensor-observation-derived representation of at least one sensor observation subject that is one member of at least one specific group of sensor observations subjects, and (c) cyber determinations of the point or points where at least one selected measure point will be located on at least one sensor-observation-derived representation of at least one sensor observation subject from a spectrum of sensor observation subjects.

In some embodiments of the platform the spectrum of subjects of sensor observations includes at least one person as at least one sensor observation subject;

wherein at least one analytically rich aspect, characteristic or feature of the at least one person includes at least one aspect, characteristic or feature selected from a spectrum of analytically rich aspects, characteristics or features of people who are subjects of sensor observations;

wherein at least one measure point is utilizable in the locating of at least one selected analytically rich aspect, characteristic or feature of or from at least one sensor-observation-derived representation of at least one person;

wherein the at least one measure point is utilizable for at least one purpose selected from a spectrum of purposes for which measure points that are utilized in the locating of selected analytically rich aspects, characteristics or features of or from sensor-observation-derived representations of people may be utilized;

wherein the spectrum of analytically rich aspects, characteristics or features from sensor-observation-derived representations of people includes (a) scars, (b) marks, (c) tattoos, (d) fingerprint features, (e) axis points at joints, (f) tip of nose, (g) corners of eyes, (h) centers of pupils, (i) corners of mouth, (j) tips of fingers, (k) sweat glands, (l) coughs, (m) tremors, (n) shivers, or (o) any other analytically rich aspects, characteristics or features of or from sensor-observation-derived representations of people.

The platform is further configurable for making at least one selected cyber determination regarding or utilizing the at least one sensor observation or the at least one sensor observation subject, wherein the at least one sensor observation is made (a) at one or more points in time, or (b) over one or more periods of time, and the concise datasets platform includes, in at least one concise dataset, at least one informational representation regarding or utilizing at least one selected analytically rich change that occurs over at least one period of time to at least one sensor-observable aspect, characteristic or feature of or from the at least one sensor observation or the at least one sensor observation subject.

The platform is further configurable for the at least one subject of the at least one sensor observation to be at least one person, and wherein at least one analytically rich change that occurs over at least one period of time is at least one change to at least one sensor observable aspect, characteristic or feature of the at least one person selected from the group consisting of sensor-observable analytically rich changes that occur over time to aspects, characteristics or features of a person's (a) head, (b) face, (c) mouth, (d) eyes, (e) eyebrows, (f) nose, (g) arms, (h) hands, (i) fingers, (j) legs, (k) feet, (l) neck, (m) torso, (n) skin, (o) heart, (p) stomach, (q) intestines, (r) liver, (s) kidneys, (t) lungs, (u) breath, (v) vascular system, (w) brain, (x) spinal cord, (y) neural system, (z) neural activity, (aa) skeleton, (bb) blood, (cc) odor, (dd) voice, (ee) movement, (ff) tip of nose, (gg) corners of eyes, (hh) centers of pupils, (ii) axis points at joints, or (jj) any aspects, characteristics or features of a person selected from a spectrum of other aspects, characteristics or features of a person where analytically rich sensor-observable changes may occur over time.

The platform is further configurable for at least one selected cyber determination to include at least one determination of an indicated measure of probability that exists of one specific yet-to-be-identified person being the same person as one specific known person, wherein the at least one cyber determination ranges from the making of at least one cyber determination that one specific, yet-to-be-identified person absolutely is not one specific known person, through the making of at least one cyber determination of any intermediate indicated measure of probability that exists of one specific, yet-to-be-identified person being one specific known person, to the making of at least one cyber determination that one specific yet-to-be-identified person absolutely is one specific known person.

The platform is further configurable for making at least one selected cyber determination that is utilized in the process of accurately or reliably granting or denying, at least one person or at least one cyber device, access to at least one member selected from the group consisting of (a) all or part of the concise datasets platform, (b) all or part of at least one resource that is being utilized by the concise datasets platform, or (c) all or part of at least one resource that is utilizing the concise datasets platform.

The platform is further configurable for being utilized in the accurate or reliable cyber testing of the identity of at least one specific person, wherein at least one concise datasets platform enabled cyber identity test may be configured to utilize at least one selected level of identity test participation by at least one person who is at least one subject of at least one cyber identity test, and wherein the at least one selected level of participation ranges from the at least one person being observable by at least one sensor but not consciously engaged in the at least one cyber identity test, to the at least one person being an observable, active and consciously engaged participant in the at least one cyber identity test.

The platform is further configurable for including cyber identity test repeating operations wherein at least one part of at least one first series observation of one specific known person is selected to be repeated by one specific yet-to-be-identified person, wherein the one specific yet-to-be-identified person performs at least one selected repetition, wherein the concise datasets platform assigns at least one appropriate informational representation regarding or utilizing at least one member selected from the group consisting of (a) the at least one observation, (b) the at least one repetition, or (c) at least one analytically rich aspect, characteristic or feature of or from the one specific yet-to-be-identified person while the yet-to-be-identified person is performing the repetition, wherein the at least one second series observation concise dataset of the at least one repetition includes at least one informational representation that was appropriately assigned to the repetition by the concise datasets platform, and wherein the at least one second series observation concise dataset from the at least one repetition is utilizable in the making of at least one selected cyber determination regarding or utilizing the identity of the yet-to-be-identified person.

The platform is configurable for being utilized as at least one universal health metrics monitor, wherein the at least one universal health metrics monitor is configured for monitoring or recording at least one selected part of at least one sensor observation of at least one selected analytically rich aspect, characteristic or feature of the health of at least one person; the universal health metrics monitor is further configurable for making or reporting on at least one selected cyber determination regarding or utilizing at least one selected sensor-observed analytically rich aspect characteristic or feature of the health of a person;

wherein the at least one cyber determination is selected from a spectrum of health-related cyber determinations that may be made regarding or utilizing health-related analytically rich aspects, characteristics or features of or from sensor observation-derived representations of people;

wherein the spectrum of cyber determinations regarding or utilizing health-related analytically rich aspects, characteristics or features of or from sensor observation-derived representations of people includes at least one cyber determination that identifies at least one health-related tell regarding or utilizing at least one analytically rich aspect, characteristic, or feature of or from at least one sensor observation-derived representations of a person, wherein the at least one health-related tell accurately or reliably indicates, in whole or in part, that a person has, had or will have at least one selected health-related occurrence that the person may, should or does want to utilize or be made aware of;

wherein the at least one tell is from a spectrum of sensor-observable tells regarding or utilizing the health of people;

wherein the at least one health-related tell is utilizable by the universal health metrics monitor in the making of at least one selected cyber determination regarding or utilizing at least one selected sensor-observed analytically rich aspect characteristic or feature of the health of a person;

wherein the at least one selected cyber determination is utilizable by the universal health metrics monitor in the monitoring of, or reporting on, selected aspects, characteristics, or features of or from a person's health;

wherein the monitoring or recording operations of the universal health metrics monitor may be made (a) as a one-time single event, (b) intermittently, or (c) constantly;

wherein reporting operations of universal health metrics monitors are configurable for the making of at least one selected report regarding or utilizing at least one health-related analytically rich aspect, characteristic or feature of or from at least one sensor-observation-derived representation of a person selected from a spectrum reports that may be made regarding or utilizing health-related analytically rich aspect, characteristic or feature of or from sensor-observation-derived representations of people;

wherein the recording is made of all or part of at least one selected sensor observation dataset; wherein at least one person or the universal health metrics monitor selects the all or the part of the at least one selected sensor observation dataset that is to be recorded;

wherein the universal health metrics monitor is configurable for including the selected all or the selected part of the at least one sensor observation dataset as selected sensor data in at least one concise dataset;

wherein the at least one sensor observation is made at one or more points in time or over one or more periods of time;

wherein the any other necessary resources include at least one sensor that is utilizable by the universal health metrics monitor in the capturing of at least one selected sensor observation of at least one selected analytically rich aspect, characteristic or feature of a person's health;

wherein the at least one sensor is selected from a spectrum of sensors that may be utilized in the capturing of analytically rich health-related observations of a person;

wherein the spectrum of sensors includes (i) internal sensors, (ii) external sensors, (iii) wearable sensors, (iv) sensors that are in the observable proximity of a person who is a subject of a sensor's observation, or (v) any other sensors that are utilizable in the making of at least one selected cyber determination regarding or utilizing the health of a person.

The platform is configurable for being utilized in the making of one or more selected one-time single event health-related cyber test determinations regarding or utilizing at least one selected sensor-observed analytically rich aspect, characteristic or feature of the health of a person;

wherein the selected one or more one-time single event health-related cyber test determinations may be made or utilized in real time or at one or more times thereafter;

wherein the selected one or more one-time single event health-related cyber test determinations are made utilizing at least one sensor selected from a spectrum of sensors that are utilized in the making of one-time single event health-related cyber test determinations regarding or utilizing selected sensor-observable analytically rich aspects, characteristics or features of the health of a person;

wherein the at least one selected analytically rich aspect, characteristic or feature of the health of a tested person is from a spectrum of sensor-observable analytically rich aspects, characteristics or features of the health of people;

wherein the spectrum of health-related cyber test determinations regarding or utilizing selected sensor-observable analytically rich aspects, characteristics or features of the health of a person include test determinations regarding the presence of (a) COVID-19, (b) H1N1, (c) Ebola, (d) cancer, or (e) any other selected aspects, characteristics or features of a person's health that can be sensor-observed, tested and accurately or reliably reported upon;

wherein the one-time single event health-related cyber test determinations regarding or utilizing at least one selected sensor-observed analytically rich aspect, characteristic or feature of the health of a person may be utilized for at least one purpose selected from a spectrum of purposes for which one-time health-related cyber test determinations regarding or utilizing sensor-observed analytically rich aspects, characteristics or features of the health of a person may be utilized;

wherein the spectrum of purposes for which one-time health-related cyber test determinations regarding or utilizing sensor-observed analytically rich aspects, characteristics or features of the health of a person may be utilized includes the purpose of making at least one health-related cyber test determination regarding or utilizing at least one selected sensor-observed analytically rich aspect, characteristic or feature of the health of a person prior to or immediately prior to the tested person being granted or denied access to at least one member selected from the group consisting of (a) schools, (b) public transportation, (c) houses of worship, (d) workplaces, (e) events, (f) sporting activities, (g) restaurants, (h) bars, (i) stores, (j) hospitals, (k) parks, (l) prisons, (m) nursing homes, (n) grocery stores, (o) theaters, (p) gyms, (q) health care providers offices, (r) concerts, (s) salons, (t) meat processing plants, or (u) any other places or activities where it may be required or desired to determine if one specific tested person does or does not have at least one selected health-related aspect, characteristic or feature that would or should exclude the specific tested person from gaining initial access or having continued access to the places or activities.

The concise datasets platform is further configurable for utilizing at least one measure point in the locating of at least one sensor-observation-derived representation of at least one selected analytically rich aspect, characteristic or feature of or from at least one sensor-observation-derived representation of at least one face of at least one person;

wherein the at least one measure point is utilized for at least one purpose selected from a spectrum of purposes for which measure points that are utilized in the locating of analytically rich aspects, characteristics or features of or from sensor-observation-derived representations of faces of people may be utilized;

wherein the spectrum of purposes for which measure points that are used in the locating of analytically rich aspects, characteristics or features of or from sensor-observation-derived representations of faces of people may be utilized includes utilizing at least one measure point for (a) determining the identity of a yet-to-be-identified person, (b) authenticating the claimed identity of a yet-to-be-identified person, (c) determining a person's facial affect, (d) determining a person's facial expression, (e) determining the gaze of a person's eye or eyes, (f) determining sensor or camera angle, (g) determining sensor observation lighting circumstances, (h) determining a person's pose, (i) determining a portion of a person's face that is being observed, (j) determining at least one measure of a person's state of the mental or physical health, (k) determining a person's pulse rate, (l) determining a person's blood pressure, (m) determining at least one relationship between at least one sensor and at least one measure point that is located on at least one sensor-observation-derived representation of a person's face, or (n) for any other purpose selected from a spectrum of other purposes for which measure points that are used in the locating of selected analytically rich aspects, characteristics or features of or from sensor-observation-derived representations of people's faces may be utilized.

The platform is configurable for the making of at least one selected cyber determinations regarding or utilizing at least one measured location of or at least one measured orientation of at least one selected analytically rich aspect, characteristic or feature of or from at least one sensor-observation-derived representation of at least one person;

wherein the at least one sensor-observation-derived representation of the at least one analytically rich aspect, characteristic or feature of the at least one person is selected from a spectrum of sensor-observation-derived representations of analytically rich aspects, characteristics or features of or from people who are subjects of sensor observations;

wherein at least one measured location of, or at least one measured orientation of the at least one selected analytically rich aspect, characteristic or feature of or from the at least one sensor observation derived representation of the at least one person includes, for example, the measured location of, or the measured orientation of (a) at least one sensor-observation-derived representation of at least one fingerprint feature on at least one sensor-observation-derived representation of a finger or a fingerprint of a person, (b) at least one sensor-observation-derived representation of at least one tattoo on at least one sensor-observation-derived representation of a person, (c) at least one sensor-observation-derived representation at least one scar on at least one sensor-observation-derived representation of a person, (d) at least one sensor-observation-derived representation of at least one mark on at least one sensor-observation-derived representation of a person, (e) at least one sensor-observation-derived representation of at least one sweat gland on at least one sensor-observation-derived representation of a person, (f) at least one sensor-observation-derived representation of at least one pulse point on at least one sensor-observation-derived representation of a person, or (g) any other sensor-observation-derived representations of analytically rich aspects, characteristics or features of a person selected from a spectrum of sensor-observation-derived representations of analytically rich aspects, characteristics or features of people.

The platform is configurable for utilizing at least one measure point in the locating of at least one sensor-observation-derived representation of the tip of at least one finger of at least one person;

wherein the at least one measure point is utilized for at least one purpose selected from a spectrum of purposes for which measure points that are utilized in the locating of sensor-observation-derived representations of people's fingertips may be utilized;

wherein the spectrum of purposes for which measure points that are utilized in the locating of sensor-observation-derived representations of people's finger tips are utilized includes utilization as at least one component of at least one fingertip-to-cyber device touchless user interface; and wherein the at least one cyber device is at least one type of cyber device selected from a spectrum of types of cyber devices that may utilize at least one fingertip-to-cyber device touchless user interface.

The platform is configurable for utilizing at least one measure point in the locating of at least one selected analytically rich aspect, characteristic or feature from at least one sensor-observation-derived representation of at least one person for utilization as at least one component of at least one human-to-cyber device touchless user interface;

wherein the at least one human-to-cyber device touchless user interface, using the at least one measure point, is utilized for at least one purpose selected from a spectrum of purposes for which human-to-cyber device touchless user interfaces may be utilized; and wherein the at least one cyber device is at least one type of cyber device selected from a spectrum of types of cyber devices that may utilize at least one human-to-cyber device touchless user interface.

The platform is configurable for utilizing at least one measure point in the locating of at least one axis point from at least one sensor-observation-derived representation of at least one joint of at least one person;

wherein the at least one measure point that locates the at least one axis point is utilized for at least one purpose selected from a spectrum of purposes for which measure points that locate sensor-observation-derived representations of axis points of joints of people may be utilized; and wherein the spectrum of purposes for which measure points that are utilized in the locating of sensor-observation-derived representations of axis points of joints of people may be utilized includes (a) the making of at least one selected cyber determination regarding or utilizing the geometry of the at least one sensor-observation-derived representation of the at least one joint, or (b) the making of at least one selected cyber determination that utilizes the at least one measure point in the locating of the at least one axis point on the at least one sensor-observation-derived representation of the at least one joint of the at least one person for at least one purpose from a spectrum of other purposes for which measure points that locate axis points of joints from sensor-observation-derived representations of people may be utilized.

The platform is configurable for being utilized in the making of at least one selected cyber determination regarding or utilizing at least one analytically rich aspect, characteristic or feature of the geometry of at least one sensor-observation-derived representation of at least one joint of at least one person; and wherein the at least one selected analytically rich aspect, characteristic or feature of the geometry of the at least one sensor-observation-derived representation of at least one joint of at least one person is utilized for at least one purpose selected from a spectrum of purposes for which analytically rich aspects, characteristics or features of the geometry of sensor-observation-derived representations of joints of people may be utilized.

(19) The platform is configurable for utilizing at least one measure point in the making of at least one selected measurement;

wherein the at least one selected measurement that is made through utilization of the at least one measure point is selected from a spectrum of measurements that may be made through use of measure points that are utilized in the locating of selected analytically rich aspects, characteristics or features of or from sensor-observation-derived representations; and wherein the spectrum of measurements that may be made through utilization of the at least one measure point include (a) measured distances between two or more measure points, (b) measured angles where two or more lines between measure points meet or intersect, (c) measured location of at least one measure point, aspect, characteristic or feature, (d) measured orientation of at least one measure point, aspect, characteristic or feature, (e) measured relationships between two or more measure points, aspects, characteristics or features, (f) time of capture of a sensor observation, (g) measured pressure at, or in the area of one or more measure points, (h) measured temperature at, or in the area of one or more measure points, (i) measured observed level of colored light at, or in the area of one or more measure points, (j) measured grey scale level at, or in the area of one or more measure points, (k) measured odor at, or in the area of one or more measure points, (l) measured presence at, or in the area of one or more measure points, (m) measured sound at, or in the area of one or more measure points, (n) measured energy at, or in the area of one or more measure points, (o) measured chemical presence at, or in the area of one or more measure points, or (p) measures of any other measurable sensor-observable analytically rich aspects, characteristics or features of or from sensor-observation-derived representations that may be located through utilization of measure points.

The platform is configurable for any of its operations or any part thereof to be performed in any usable order or sequence.

The platform is configurable for achieving at least one selected attainable level of accuracy goal for at least one selected cyber determination, and the at least one attainable level of accuracy goal falls in a range extending from 0% accuracy up to and including 100% accuracy.

The platform is configurable for utilizing information or informational representations that are from at least one source other than at least one first series observation, or at least one second series observation.

The platform is configurable for manipulating, in any way possible, the operations of concise datasets platform utilized resources, or any part of the concise datasets platform itself, wherein manipulating provides the concise datasets platform with selections of possible utilizations, wherein the manipulating is utilized for at least one purpose selected from a spectrum of purposes for which the manipulating can be utilized, wherein the spectrum of purposes for said manipulating includes the purpose of aiding in the making of at least one selected cyber determination.

The platform is configurable for at least one sensor observation dataset from at least one source that is not at least one first series observation operation to be included as at least one part of at least one first series observation dataset, or wherein at least one part of at least one observation dataset from at least one source that is not at least one second series observation operation to be included as at least one part of at least one second series observation concise dataset.

The platform is configurable for including platform history, wherein the platform history is comprised of at least one platform history record.

The present disclosure further pertains to a platform that is comprised of computing devices, sensors, cyber processes and cyber procedures that are utilized for capturing, selecting, deriving or utilizing data for or from concise datasets, wherein the data for or from the concise datasets is utilizable in the making of at least one selected cyber determination regarding or utilizing at least one sensor observation or at least one sensor observation subject, the concise datasets platform is further comprised of: deriving or utilizing information from at least one point in time or from at least one period of time from a spectrum of information that includes at least one observed aspect, characteristic or feature of or from at least one sensor observation or at least one subject of at least one sensor observation, thereby obtaining sensor-derived information;

wherein the at least one sensor observation is a type of sensor observation selected from the group consisting of (a) visual sensor observations, (b) audible sensor observations, (c) thermal sensor observations, (d) olfactory sensor observations, (e) tactile sensor observations, (f) chemical sensor observations, or (g) any other types of sensor observations selected from a spectrum of other types of sensor observations that may be utilized by the concise datasets platform;

wherein the concise datasets platform captures, selects, derives or utilizes data for or from concise datasets, or makes at least one selected cyber determination through the utilization of (a) at least one computing device, (b) at least one sensor, (c) necessary programming, (d) the information, (e) criteria that are utilized by the concise datasets platform, and (f) any necessary resources;

wherein the concise datasets platform makes at least one selected cyber determination type from the group consisting of (i) one-time single event cyber determinations, (ii) intermittently made cyber determinations, or (iii) constantly made cyber determinations;

wherein the at least one selected cyber determination is utilized for at least one purpose; and wherein the concise datasets platform further comprises utilizing at least one part of at least one operation selected from the group consisting of
 (a) first series observation operations wherein the concise datasets platform utilizes at least one sensor observation, wherein the at least one sensor observation or at least one subject of the at least one sensor observation has at least one previously determined aspect, characteristic or feature, the concise datasets platform recognizes the at least one aspect, characteristic or feature, the at least one recognized aspect, characteristic or feature is utilizable by the concise datasets platform in the making of at least one selected cyber determination, the concise datasets platform assigns appropriate informational representations regarding at least one known aspect, characteristic or feature of the at least one sensor observation or the at least one sensor observation subject, the concise datasets platform includes at least one of the informational representations in at least one first series observation concise dataset,
 (b) second series observation operations wherein the concise datasets platform utilizes at least one sensor observation, and wherein the at least one sensor observation or at least one subject of the at least one sensor observation has at least one yet-to-be-determined aspect, characteristic or feature, the concise datasets platform recognizes the at least one yet-to-be-determined aspect, characteristic or feature, the concise datasets platform assigns appropriate informational representations regarding the at least one yet-to-be-determined aspect, characteristic or feature of the at least one sensor observation or the at least one sensor observation subject, wherein the concise datasets platform includes at least one of the informational representations in at least one second series observation concise dataset, (c) measure point operations, wherein the concise datasets platform utilizes at least one measure point in the locating of at least one selected analytically rich aspect, characteristic or feature of or from at least one sensor-observation-derived representation of at least one sensor observation or at least one sensor observation subject, wherein the concise datasets platform assigns at least one appropriate informational representation regarding the at least one measure point, aspect, characteristic or feature of or from the at least one sensor-observation-derived representation, wherein the at least one informational representation is stored or utilized in the making of at least one selected cyber determination regarding or utilizing the at least one sensor observation or the at least one sensor observation subject, (d) concise datasets operations, wherein the concise datasets platform utilizes at least one concise dataset in the making of at least one selected cyber determination, the at least one concise dataset includes selected sensor data or selected derived data, wherein the selected sensor data is comprised of at least one informational representation that was selected from the informational representations of at least one sensor observation dataset, and wherein the selected derived data is comprised of at least one informational representation that was derived from the processing of at least one selected informational representation from the original sensor observation dataset, or from the processing of at least one selected informational representation from derived data, wherein at least one informational representation from the selected sensor data or at least one informational representation from the selected derived data is utilizable by the concise datasets platform in the making of at least one selected cyber determination regarding or utilizing at least one sensor observation or at least one sensor observation subject, and wherein the selected derived data is derived utilizing at least one method or formula selected from a spectrum of methods or formulas that may be utilized in the deriving of at least one informational representation from sensor data or derived data, (e) matching operations, wherein the concise datasets platform's matching operations include matching at least one informational representation from at least one second series observation concise dataset with at least one informational representation from at least one comparable first series observation concise dataset, (f) comparing operations, wherein the comparing operations include the concise datasets platform's comparing of informational representation from at least one second series observation concise dataset with comparable informational representation from at least one first series observation concise dataset, and providing at least one conclusion or determination from the comparison, (g) determining operations, wherein the concise datasets platform utilizes at least one conclusion or determination from at least one comparing operation or information in the making of the at least one selected cyber determination, or (h) reporting operations, wherein the concise datasets platform's operations include the making of at least one selected report regarding or utilizing at least one aspect, characteristic or feature of at least one part of at least one cycle of utilization of the concise datasets platform.

BRIEF DESCRIPTION OF THE DRAWING

FIG. 1 is an illustration of a particular non-limiting embodiment of operations of the platform and its associated cyber processes or procedures in accordance with the teachings herein.

DETAILED DESCRIPTION

The present disclosure pertains to a scalable configurable universal full spectrum platform that is configurable for making selected cyber determinations regarding or utilizing sensor observations or sensor observation subjects. The platform includes at least one computing device, predetermined criteria and necessary cyber resources, along with: (a) information, or (b) data regarding or utilizing sensor observations or sensor observation subjects for utilization in the making of one or more selected cyber determinations regarding or utilizing sensor observations or sensor observation subjects. The selected cyber determinations are from a spectrum of cyber determinations that may be made regarding or utilizing sensor observations or sensor observation subjects.

The platform is configurable for making selected cyber determinations regarding or utilizing measure points that are used in the locating of selected analytically rich aspects, characteristics or features from sensor-observation-derived representations.

The platform is configurable for assigning or utilizing informational representations regarding or utilizing measure points or analytically rich aspects, characteristics or features of or from sensor-observation-derived representations.

Additionally, the platform is configurable for utilizing concise datasets in the making of selected cyber determinations.

Unless otherwise specified herein, throughout this entire disclosure, each of the following will apply:
  (a) the platform is scalable and therefore can be scaled to include platform resources from any point in a range of included or utilized platform resources, wherein at one end of the range the platform is scaled to include or utilize the least platform resources, and at the other end of the range the platform is scaled to include or utilize all platform resources;
  (b) the platform is configurable and can be configured to be utilized in at least one configuration;
  (c) the platform is configurable for universal utilization of all or part of its processes, procedures or resources;
  (d) the platform is configurable for providing selection of criteria, wherein criteria are selected from a spectrum of criteria that are utilizable by the platform in the making of selected cyber determinations regarding or utilizing sensor observations or sensor observation subjects;
  (e) the platform is a full spectrum platform and is configurable for utilizing any processes, procedures or resources selected from a spectrum of processes, procedures, or resources that are utilizable in the making of selected cyber determinations regarding or utilizing sensor observations or sensor observation subjects. Further, the platform is configurable for providing for any cyber determination needs selected from a spectrum of needs for cyber determinations regarding or utilizing sensor observations or sensor observation subjects; and (f) an operational goal of the platform is to preferably provide a best performing blend of as simple, concise and efficient operations as possible.

The present disclosure primarily addresses the use of video-formatted image sensor observations of people, however, the platform is configurable for making selected cyber determinations regarding or utilizing any sensor observation or any sensor observation subject from a spectrum of sensor observation or sensor observation subjects.

Definitions

In the present disclosure the following terms or phrases have the meanings indicated below.

Absolutely unique: occurring at a ratio of one to the total (non-zero) number of first series observation datasets. Thus, for example, if there are 100 first series observation datasets, then an occurrence is absolutely unique if it occurs at a ratio of 1:100.

Adjusting factors: processes, procedures, methods, formulas or combinations thereof that are utilized to enable the platform to accurately or reliably make selected cyber determinations when there are observation circumstances or analytically rich aspects, characteristics or features of second series observations or second series observation subjects that are not exact matches to the observation circumstances or analytically rich aspects, characteristics or features from the first series observations or first series observation subjects with which they are being matched or compared.

Analytically rich: being usable by the platform in the accurate or reliable making of one or more selected cyber determinations regarding or utilizing sensor observations or sensor observation subjects.

Artificial intelligence/AI: the use of cyber resources that include computing devices, programs, processes, procedures or necessary data in the answering of selected questions and then utilizing the answers in the selecting of the best possible requested resources to deliver.

Aspects: at least one aspect, characteristic or feature of or from sensor-observation-derived representations of sensor observations or sensor observation subjects.

Aspects, characteristics or features: at least one member selected from the group consisting of: (a) aspects, (b) characteristics, or (c) features of or from sensor-observation-derived representations of sensor observations or sensor observation subjects.

Behavioral analysis: the use of analysis of sensor-observed behavior of biological organisms or of devices.

Biological characteristics: any biological aspects, characteristics or features of biological organisms, including people, that are sensor observable.

Camera: an image sensor; a video-formatted image sensor.

Capture/capturing: the use of cyber resources for acquiring and recording cyber sensor observations.

Characteristics: at least one aspect, characteristic or feature of or from sensor-observation-derived representations of sensor observations or sensor observation subjects.

Concise datasets: small datasets; datasets that contain little or no unnecessary data; datasets that are typically at least 90% smaller than the original sensor observation dataset from which the concise datasets were selected or derived; datasets that are comprised of analytically rich sensor observations or sensor-observation-derived data.

Constant determinations: cyber determinations that are made at any frequency that essentially results in the continuous making of cyber determinations.

Criteria: a group of selectable options containing at least one member.

Cyber: utilizing non-biological processing of programming; the term includes anything (such as, for example, devices, programming, processes or files) that utilize or are utilized for non-biological processing of programming in any way.

Cyber determinations: one or more questions regarding or utilizing sensor observations or sensor observation subjects that are answered through utilization of cyber resources.

Cyber portals: cyber devices that are configured to perform at least one action selected from the group consisting of: (a) sending cyber interactions from a person who is using a cyber portal, (b) receiving cyber interactions that are sent to a cyber portal, (c) providing sensor observations of a person who is using a cyber portal for use in determining the identity of the person who is using the cyber portal, or for use for any other purposes, (d) providing output to a user that enables the user to perceive cyber interactions that are sent to a cyber portal, or (e) enabling a person to interact with cyber devices or with cyber interactions that are sent to a cyber portal.

Cyber resources: at least one cyber asset or at least one cyber resource.

Digitation: at least one fingertip that is observed by sensors and used by a person to communicate the person's intent to interact with cyber resources.

Derived data: data that are derived from the processing of selected sensor data or other selected derived data.

Determinations of identity: cyber determinations of previously unknown identity or cyber determinations for authenticating or verifying claimed identity.

Enrolling/enrollment: the initial collecting or processing of sensor observations of one specific enrollee, wherein the processing results in the assignment of the appropriate informational representations that make up the initial first series observation concise datasets (the cyber identity or identifiers) for the one specific enrollee; informational representations from enrollment are utilized as at least one part of the first series observation concise datasets of the one specific observation subject that is the enrollee.

Feature: at least one aspect, characteristic or feature of or from sensor-observation-derived representations of sensor observations or sensor observation subjects.

Final cyber determination: the last cyber determination in a structured series of cyber determinations.

Finger: a finger or a thumb.

Frame: a single video-formatted image that is a part of a stream of sequential video-formatted images.

Full spectrum: the complete set of possible choices for a given variable or option which includes the subset of available choices for any given variable or option; thus, for example, the full spectrum of cyber resources is the complete set of possible cyber resources, which includes all available cyber resources.

Identity determinations: cyber determinations regarding identity.

Indicators: analytically rich aspects, characteristics or features from sensor-observation-derived representations that are assigned appropriate informational representations and then stored for utilization in the making of selected cyber determinations.

Informational representations: designations, names, labels or measurements that are appropriately assigned to sensor-observed analytically rich aspects, characteristics or features of or from sensor-observation-derived representations of sensor observations or sensor observation subjects.

Initial cyber determination: the first in a series of questions to be answered through the use of cyber resources.

Intermediate cyber determination: any cyber determinations that are utilized in the answering of selected questions that are not exclusively the initial cyber determination or the final cyber determination from a selected or structured series of cyber determinations.

Known person: a person who is the known subject of at least one first series observation concise dataset.

Machine learning: the use of cyber resources for the making of at least one cyber determination, wherein the at least one cyber determination is then utilized to improve upon or further refine the results of at least one subsequent cyber determination; machine learning may be structured or unstructured; structured machine learning utilizes a structured sequence of processes or procedures; structured machine learning can be diagnosed, repaired or altered if it is not performing as intended; unstructured machine learning uses processes or procedures that are unknown to humans because they were selected by the machine learning process and performed with no record of the intermediate cyber determinations or the final cyber determinations that were made; typically it is not possible to diagnose and repair unstructured machine learning processes when they are not performing as intended.

Measure points: markers that are utilized in the locating of selected analytically rich aspects, characteristics or features from sensor-observation-derived representations; measure points are utilized as a reproducible structure from which: (a) measurements are made or, (b) structured analysis is done to sensor-observation-derived representations of sensor observations or sensor observation subjects.

Multitude: a quantity that is more than 100.

One time/one-time: occurring at only one specific point in time, or only over one short period of time.

Point: the smallest addressable location from a sensor observation-derived representation.

Physical analysis: the utilization of analysis of sensor-observable physical aspects, characteristics or features of sensor observation subjects.

Physiological analysis: the utilization of analysis of sensor-observable physiological aspects, characteristics or features of sensor observation subjects.

Platform: concise datasets platform.

Real time/real-time: occurring at essentially the exact moment in time that a sensor observation is captured; occurring at a time that was so close to the time when a sensor observation was captured that a person would not notice latency.

Recognized: analytically rich aspects, characteristics or features from sensor-observation-derived representations that are accurately or reliably identified for further utilization.

Selected cyber determinations: selected cyber determinations regarding or utilizing sensor observations or sensor observation subjects.

Series: a group of at least one.

Smudge/smudges: sensor observed artifacts of prior light that were fully present at previous points in time; wherein the artifacts of prior light are recognizable parts of sensor-observation-derived representations; prior light from previous points in time (possibly in increments of 500 points in time or more per second) can still be captured by the sensor for one or more points in time past the final point in time when the sensor-observed-representation of the fully present light was captured; analysis of the artifacts can then be utilized in the making of selected cyber determinations regarding or utilizing what occurred at one or more points in time prior to when an image was captured; the artifacts can also be utilized in the making of selected cyber predictions of what will be observed in the future; smudges can also be reflected or refracted light that alters the observed levels of colored light at pixels that adjoin or are in the area of the sources of refracted or reflected light.

Smudge analysis: the utilization of analysis of smudges or irregularities from sensor-observation-derived representations.

Spectrum: a full spectrum; a complete set of possible choices for a given variable or option.

Tells: analytically rich aspects, characteristics or features of or from sensor-observation-derived representations that are utilizable in the accurate or reliable making of one or more selected cyber determinations.

Unique: occurring at a selected ratio other than the ratio of absolutely unique.

Unique biological aspects, characteristics or features: any single observable aspect, characteristic or feature of a biological organism or any combination of observable aspects, characteristics or features of one biological organism (e.g., a biological fingerprint) that is considered to be unique or absolutely unique to the one specific observed biological organism.

Video cameras: video-formatted image sensors.

Visual analysis: the analysis of images from image-sensor-observation-derived representations.

Y: a vertical line or line location from a pixel grid.

Yet-to-be-identified person: one specific person who is a subject of a second series observation; one specific person who has not yet been determined to be the same person as one specific known person.

X: a horizontal line or line location from a pixel grid.

Prior Art's Problems

Prior art's inability to fulfil the world's needs for accurate or reliable real-time cyber determinations regarding or utilizing sensor observations or sensor observation subjects is due in part to the numerous limitations and inefficiencies of prior art and its processes or procedures.

Prior art processes or procedures for making selected cyber determinations regarding or utilizing sensor observations or sensor observation subjects have many, if not all, of the following problems or inefficiencies:

a. prior art requires a great deal of analysis or comparison in the making of each initial, intermediate or final cyber determination;

b. datasets from prior art can only be utilized in the making of one selected final cyber determination during each cycle of prior art's processing operations;

c. datasets from prior art processes are large and therefore inefficient to store, manage or compare;

d. datasets from prior art are not interoperable and therefore the datasets from one prior art process cannot be universally used with any or all other prior art processes;

e. prior art must reprocess second series sensor observation datasets each time they are compared to a different first series sensor observation dataset;

f. prior art is not universally usable across a spectrum of sensor observation circumstances, wherein sensor observation circumstances include: lighting, pose, sensors utilized, positions of subjects relative to the sensors, movements of sensors or sensor observation subjects, temperature, wind conditions, items on or around sensor observation subjects, other subjects of the sensor observation, location or any other sensor observation circumstances selected from a spectrum of sensor observation circumstances;

g. prior art does not utilize all of the analytically rich aspects, characteristics or features from sensor observations that are needed for achieving the highest attainable levels of accuracy when making selected cyber determinations regarding or utilizing sensor observations or sensor observation subjects;

h. prior art cannot utilize the spectrum of types of sensor observations or the spectrum of sensor-observable analytically rich aspects, characteristics or features of sensor observations or sensor observation subjects;

i. prior art is not scalable or configurable;

j. prior art cannot provide 100% accurate cyber determinations regarding the identity of any one specific person;

k. prior art cannot be utilized for constantly making accurate cyber determinations regarding the claimed identity of any one specific person;

l. prior art is not configurable for making cyber determinations regarding or utilizing a spectrum of analytically rich aspects, characteristics or features of a spectrum of sensor observations or a spectrum of sensor observation subjects;

m. prior art does not provide best possible performance for any aspects of its operations;

n. prior art is not as concise as it can possibly be in any aspects of its operations;

o. prior art is not as efficient as it can possibly be in any aspects of its operations;

p. prior art is not as simple as it can possibly be in any aspects of its operations;

q. prior art lacks the structure that is needed for its operations to be as concise, efficient and simple as they could possibly be in any or all areas of operations;

r. prior art does not have or use the universal processes or procedures that are needed to achieve the highest attainable levels of interoperability in the making of selected cyber determinations regarding or utilizing sensor observations or sensor observation subjects;

s. prior art does not convert selected analytically rich aspects, characteristics or features from sensor-observation-derived representations into standard concise informational representations that may be stored or used in the making of selected cyber determinations;

t. prior art does not have or utilize concise datasets to enable prior art to accurately or reliably make one or more selected cyber determinations without the need for repetitive processing or complex analysis of sensor observations, sensor observation subjects or sensor observation datasets;

u. prior art is not configured for making a spectrum of selected cyber determinations regarding or utilizing sensor observations or sensor observation subjects;

v. prior art cannot provide the vast number of real-time cyber determinations regarding or utilizing sensor observations or sensor observation subjects that are needed for the operations of autonomous vehicles or autonomous devices;

w. prior art machine learning is not structured or configured to make selected cyber determinations and to also provide reports, when needed, regarding why machine learning is not performing as intended;

x. prior art cannot be configured to use: (i) multiple sensors, (ii) multiple types of sensors, (iii) sensors in multiple environments, or (iv) sensors under multiple operational circumstances;

y. prior art that is utilized for making selected cyber determinations regarding or utilizing video-formatted image sensor observations or sensor observation subjects requires the processing of first series observation datasets and second series observation datasets each time a comparison is made of a second series observation to a first series observation;

z. prior art cannot simultaneously make a large number of differing real-time cyber determinations regarding or utilizing analytically rich aspects, characteristics or features from sensor-observation-derived representations;

aa. prior art is not configurable for utilizing more than one sensor or more than one type of sensor;

bb. prior art is not structured so that the informational representations that are a product of its operations are interoperably useable with other art that is utilized for making selected cyber determinations regarding or utilizing sensor observations or sensor observation subjects;

cc. prior art machine learning is far from being as simple, concise and efficient as it can possibly be, in part because prior art fails to recognize and not repeat any useless intermediate cyber determinations that the machine learning process makes during each learning cycle of its operations;

dd. prior art does not separate the operations of processing sensor observations from the operations of making selected final cyber determinations regarding or utilizing sensor observations or sensor observation subjects;

ee. prior art does not create, for further utilization, concise datasets that are the results of its processing of sensor observations;

ff. prior art is not configured to use concise datasets in the making of selected cyber determinations;

gg. prior art is configured to utilize complete original sensor observation datasets for all aspects of the making of selected final cyber determinations regarding or utilizing sensor observations or sensor observation subjects; this results in the use of extremely large datasets; these datasets require large amounts of storage and are difficult if not impossible to utilize in their entirety for the making of selected cyber determinations. Further, prior art utilizes datasets that are so large that significant processing resources are needed for prior art to constantly provide cyber determinations regarding the identity of any one specific person (determinations that would be less than 100% accurate);

hh. prior art fails to derive, from the processing of sensor observations, the intermediate cyber determinations that are needed for the making of 100% accurate final cyber determinations regarding the exact identity of any one specific person; and ii. each prior art uses its own processes or procedures in its making of selected cyber determinations regarding or utilizing sensor observations or sensor observation subjects; these processes or procedures cannot be interoperably used with other prior art in the other prior art's making of selected cyber determinations regarding or utilizing sensor observations or sensor observation subjects.

Prior art falls far short of providing a best performing blend of as simple, concise and efficient as possible. In many ways, prior art provides the worst performing blend of as complex, bloated and inefficient as it could possibly be in some or in all aspects of its operations.

This worst performing blend is due, at least in part, to prior art's failure to employ structure that is derived from the use of measure points that locate selected analytically rich aspects, characteristics or features of or from sensor-observation-derived representations. Doing so would allow for extreme analysis to be made of the sensor-observation-derived representations at selected points or areas that are located through utilization of the measure points.

Prior art's methodologies that utilize analysis of an entire image-based sensor observation are much more complex and computationally intensive than utilization of concise datasets would be in the making of the same selected cyber determinations.

In light of the foregoing, the platform is configurable for filling unanswered needs that presently exist with prior art—unanswered needs for selected cyber determinations regarding or utilizing sensor observations or sensor observation subjects that include:

(a) constantly making selected cyber determinations regarding whether or not a specific known person and a specific yet-to-be-identified person are the same person at any selected attainable level of accuracy, including 100% accuracy;

(b) utilizing any necessary number of analytically rich aspects, characteristics or features of one specific known person or one specific yet-to-be-identified person in the making of cyber determinations regarding the identity of the one specific yet-to-be-identified person;

(c) utilizing sensor observations of people who are not consciously engaged participants in cyber identity tests;

(d) the making of at least one member selected from the group consisting of: (i) one-time single event cyber determinations of identity, (ii) intermittently provided cyber determinations of identity, or (iii) constantly provided cyber determinations of identity, regarding people who are subjects of sensor observations;

(e) utilizing sensor observations of a yet-to-be-identified person performing a repetition of selected portions of previously captured sensor observations of a known person as a part of a cyberspace identity test;

(f) utilizing informational representations regarding sensor observations or sensor observation subjects in the making of selected cyber determinations regarding or utilizing sensor observations or sensor observation subjects;

(g) utilizing analytically rich aspects, characteristics or features from sensor-observation-derived representations of a known person or a yet-to-be-identified person in the making of selected cyber determinations regarding the identity of one specific yet-to-be identified person;

(h) utilizing measure points in the locating of selected analytically rich aspects, characteristics or features of or from sensor-observation-derived representations in the making of selected cyber determinations;

(i) providing or utilizing standard processes, procedures, measurements, designations, informational representations, names or definitions for accurately or reliably representing any aspect, characteristic or feature of the platform or its operations;

(j) enabling absolute security or privacy for any information or resources that are utilized by the platform or that are utilizing the platform;

(k) utilizing selected criteria for observing, recognizing, locating measure points, assigning appropriate informational representations, storing data, measuring, matching, comparing, determining, reporting or any of the platform's other operations;

(l) making selected cyber determinations utilizing observations that were not captured utilizing the platform;

(m) utilizing useful information that was derived from sensor observations in the making of selected cyber determinations;

(n) utilizing useful information of any type from any source in the making of selected cyber determinations;

(o) utilizing appropriately assigned standard informational representations regarding or utilizing measure points, or defined points or areas of sensor-observation-derived representations that are located through the utilization of measure points; or (p) utilizing appropriately assigned informational representations regarding sensor observations or sensor observation subjects in the making of selected cyber determinations.

The following list includes a portion of the resources or features from a spectrum of resources or features that the platform is configurable for providing or including:

(a) cyber determinations regarding or utilizing some or all sensor observation subjects selected from a spectrum of subjects of sensor observations;

(b) cyber determinations regarding or utilizing some or all analytically rich aspects, characteristics or features of or from sensor-observation-derived representations selected from a spectrum of analytically rich aspects, characteristics or features of or from sensor-observation-derived representations;

(c) cyber determinations that fill some or all needs from a spectrum of needs for cyber determinations regarding or utilizing sensor observations or sensor observation subjects;

(d) cyber determinations regarding or utilizing sensor observations or sensor observation subjects that are made at one or more selected attainable levels of accuracy which can include 100% accuracy;

(e) cyber determinations that utilize some or all resources from a spectrum of available resources that are utilizable in the making of selected cyber determinations;

(f) cyber determinations regarding or utilizing sensor observations or sensor observation subjects that utilize some or all information from a spectrum of useful information;

(g) cyber determinations that utilize some or all sensor observations from a spectrum of sensor observations;

(h) cyber determinations regarding or utilizing sensor observations or sensor observation subjects that provide for selection of some or all criteria from a spectrum useful criteria;

(i) cyber determinations regarding or utilizing sensor observations or sensor observation subjects, wherein the platform utilizes: (i) standard processes, (ii) standard procedures, (iii) standard informational representations, or (iv) standard definitions, for accurately or reliably representing any analytically rich aspect, characteristic or feature of or from the operations of the platform;

(j) cyber determinations regarding or utilizing sensor observations or sensor observation subjects that are made: (i) as one-time events, (ii) intermittently, or (iii) constantly;

(k) testing of identity prior to granting or denying people or cyber devices initial or continued access to: (i) the platform itself, (ii) cyber resources that are being utilized by the platform, or (iii) cyber resources that are utilizing the platform;

(l) security or privacy, which can include absolute security or privacy, for some or all cyber resources or activities that are utilizing or are being utilized by the platform;

(m) utilization of sensor observations of any one specific person in the making of selected cyber determinations regarding the identity of the one specific person wherein the one specific person who is a subject of a sensor observation is at any one point in a range of, from being in the presence of sensors but not being consciously engaged in determination of identity observations, to being in the observable presence of sensors and being consciously engaged in determination of identity observations;

(n) scalability of included necessary platform resources, wherein the platform is configurable for including or utilizing only the platform resources that are necessary to include or utilize for selected cyber determination needs at any point in a range; wherein at the smallest end of the range, the platform is configurable for providing for the smallest of all cyber determination needs for included or utilized platform resources, and at the largest end of the range the platform is configurable for including all platform resources;

(o) ease of use in any or all phases of the platform's operations;

(p) persistence when attempting to achieve selected goals or any part thereof;

(q) utilization of observed physical, visual, behavioral, physiological, or biological analytically rich aspects, characteristics or features of or from sensor-observation-derived representations of a yet-to-be-identified person or a known person when making selected cyber determinations regarding the identity of any one specific yet-to-be-identified person;

(r) alteration of the operations of the platform itself or any resources that are being utilized by the platform, these alterations are made for any useful purpose including the purpose of aiding in the achieving of possible-to-attain cyber determination goals;

(s) utilization of useful information that was derived from any source;

(t) appropriately assigning informational representations regarding or utilizing measure points from sensor-observation-derived representations;

(u) utilization of unique combinations of simultaneously occurring analytically rich aspects, characteristics or features of or from sensor-observation-derived representations;

(v) utilization of changes that occur over time to analytically rich aspects, characteristics or features of or from sensor-observation-derived representations;

(w) utilization of combinations of observed analytically rich aspects, characteristics or features of or from sensor-observation-derived representations of sensor observations or sensor observation subjects that were observed over one or more periods of time or at one or more points in time;

(x) utilizing useful sensor observations or useful information from any source;

(y) determining or utilizing a level of cyber determination accuracy that has been achieved;

(z) determining or utilizing a measure of adequacy of available resources;

(aa) utilizing cyber resources for capturing first series observations or second series observations; or (bb) storing informational representations regarding measure points or analytically rich aspects, characteristics or features of or from sensor-observation-derived representations in concise datasets wherein the stored informational representations may be utilized in the making of selected cyber determinations.

At present we live in a technologically interconnected world where the vast spectrum of available cyber resources is ever-widening. Over time our technologically interconnected world appears to be destined to provide every possible cyber resource that humanity could ever want or need. Included in those cyber resources, and in accordance with the teachings herein, will be a scalable configurable universal full spectrum platform that utilizes measure points from sensor-observation-derived representation or concise datasets in the making of selected cyber determinations regarding or utilizing sensor observations or sensor observation subjects.

The platform is configurable for utilizing at least one member selected from the group consisting of:

(a) processes or procedures for selecting the analytically rich aspects, characteristics or features from sensor-observation-derived representations that are utilized in the making of selected cyber determinations;

(b) processes or procedures for identifying the analytically rich aspects, characteristics or features from a sensor-observation-derived representation that will be located through utilization of measure points;

(c) processes or procedures for determining the measure points that will be included as members of standard target sets of measure points, wherein the standard target sets of measure points can each be configured to be utilized in the making of selected cyber determinations regarding or utilizing selected sensor observations or selected sensor observation subjects under a specific set of, or under varying sensor observation circumstances;

(d) processes or procedures for accurately or reliably utilizing measure points in the locating of selected analytically rich aspects, characteristics or features of or from sensor-observation-derived representations;

(e) processes or procedures for assigning appropriate informational representations regarding or utilizing at least one member selected from the group consisting of: (i) measure points, (ii) analytically rich aspects, characteristics or features, (iii) sensor observations, or (iv) sensor observation subjects;

(f) processes or procedures for storing informational representations regarding or utilizing at least one member selected from the group consisting of: (i) measure points, (ii) analytically rich aspects, characteristics or features, (iii) sensor observations, or (iv) sensor observation subjects;

(g) processes, or procedures for appropriately assigning or utilizing standard informational representations regarding at least one member selected from the group consisting of: (i) measure points, (ii) analytically rich aspects, characteristics or features, (iii) sensor observations, or (iv) sensor observation subjects, in the making of selected cyber determinations; or (h) any other processes or procedures that may be utilized by the platform in the making of selected cyber determinations regarding or utilizing sensor observations or sensor observation subjects.

The disclosed concise datasets platform is configurable for making any cyber determination regarding or utilizing sensor observations or sensor observation subjects that our world could ever want or need. A further discussion of this universal concept has been disclosed in:

(a) co-pending U.S. patent application Ser. No. 16/998,868 (Aronson), filed Aug. 20, 2020, entitled "Universal Operating System", having the same inventor, which application is a continuation-in-part application of U.S. patent application Ser. No. 15/483,970 (Aronson), now abandoned, filed Apr. 10, 2017, entitled "Scalable Configurable Universal Operating System", having the same inventor, which is incorporated herein by reference in its entirety; which application is a continuation-in-part application of U.S. patent application Ser. No. 15/236,337 (Aronson), filed Aug. 12, 2016, issued as U.S. Pat. No. 9,660,996 on May 23, 2017, entitled "Point-of-Cyber-Access Cyber System", having the same inventor, which is incorporated herein by reference in its entirety; which application is a continuation-in-part application of U.S. patent application Ser. No. 14/447,283 (Aronson), filed on Jul. 30, 2014, issued as U.S. Pat. No. 9,479,507 on Oct. 25, 2016 (Aronson), entitled "Single-Point-of-Access Cyber System", having the same inventor, which is incorporated herein by reference in its entirety; which application is a continuation application of U.S. patent application Ser. No. 13/702,537 (Aronson), filed on Oct. 19, 2011, issued as U.S. Pat. No. 8,832,794 on Sep. 9, 2014 (Aronson), entitled "Single-Point-of-Access Cyber System", having the same inventor, which is incorporated herein by reference in its entirety; and (b) co-pending U.S. patent application Ser. No. 16/891,088 (Aronson), filed Jun. 3, 2020, entitled "Identity Testing Machine", now pending, having the same inventor, which is incorporated herein by reference in its entirety; which application is a continuation-in-part application of U.S. patent application Ser. No. 16/583,257 (Aronson), filed Sep. 26, 2019, issued as U.S. patent application Ser. No. 10,708,271 on Jul. 7, 2020 entitled "Scalable Configurable Universal Full Spectrum Cyberspace Identity Verification Test", having the same inventor, which is incorporated herein by reference in its entirety; which application is a continuation-in-part application of U.S. patent application Ser. No. 15/456,542, filed Mar. 12, 2017, issued as U.S. Pat. No. 10,462,139 on Oct. 29, 2019 (Aronson), entitled "Scalable Universal Full Spectrum Cyber Determining Process", having the same inventor, which is incorporated herein by reference in its entirety, which application is a continuation-in-part application of U.S. patent application Ser. No. 15/071,075 (Aronson), filed Mar. 15, 2016, issued as U.S. Pat. No. 9,635,025 on Apr. 25, 2017 (Aronson), entitled "Scalable Universal Full Spectrum Cyber Determining Machine", having the same inventor, which is incorporated herein by reference in its entirety; which application is a continuation-in-part application of U.S. patent application Ser. No. 14/857,445 (Aronson), filed Sep. 17, 2015, issued as U.S. Pat. No. 9,319,414 on Apr. 19, 2016 (Aronson), entitled "Scalable Full Spectrum Cyber Determination Process", having the same inventor, which is incorporated herein by reference in its entirety; which application is a continuation-in-part application of U.S. patent application Ser. No. 14/316,196 (Aronson), filed Jun. 26, 2014, issued as U.S. Pat. No. 9,166,981 on Oct. 20, 2015 (Aronson), entitled "Full Spectrum Cyber Identification Determination Process", having the same inventor, which is incorporated herein by reference in its entirety; which application is a continuation of U.S. patent application Ser. No. 13/784,277 (Aronson), filed Mar. 4, 2013, issued as U.S. Pat. No. 8,769,649 on Jul. 1, 2014 (Aronson), entitled "Full Spectrum Cyber Identification Determination Process", having the same inventor, which is incorporated herein by reference in its entirety; which application is a continuation of U.S. patent application Ser. No. 13/688,925 (Aronson), filed Nov. 29, 2012, issued as U.S. Pat. No. 8,434,136 on Apr. 30, 2013 (Aronson), entitled "Full Spectrum Cyber Identification Determination Process", having the same inventor, which is incorporated herein by reference in its entirety.

As the spectrum of available cyber resources continues to grow larger and larger, so does the need for concise efficient accurate real-time processes or procedures that utilize sensor observations in the accurate or reliable making of selected cyber determinations regarding or utilizing sensor observations or sensor observation subjects.

As we rely more and more on computing-based resources, one of the fundamental requirements for many of those resources is full automation of as many operations as possible. In many cases, the computing-based resources need to rely on automated real-time cyber determinations regarding occurrences in the physical world in order to accurately or reliably make the best possible cyber determinations. The platform is configurable for being a best performing blend of as simple, concise and efficient as it can possibly be throughout all of its operations, processes or procedures. The platform is configurable for doing so, in part, through utilization of measure points in the locating of selected analytically rich aspects, characteristics or features of or from sensor-observation-derived representations of sensor observation or sensor observation subjects. Use of measure points or target sets of measure points provides the structure that is needed for accurately or reliably making selected cyber determinations regarding or utilizing sensor observations or sensor observation subjects.

The platform is at least one member selected from the group consisting of: (a) configurable as a single self-contained platform, (b) configurable for utilizing interconnected resources, (c) configurable for being utilized as an integral or remote resource of devices or systems, (d) configurable for using all or part of the resources of utilized devices or systems, (e) configurable for being utilized in virtual environments or physical environments or combinations thereof, (f) configurable for being utilized by stationary devices or mobile devices or combinations thereof, (g) configurable for being utilized by devices that are located in one or more locations, or (h) configurable for utilizing or being utilized by resources that are interconnected in any way.

Best performance is preferably defined as the best possible performance or results that utilization of cyber processes, procedures or combinations thereof, can achieve. Operations of the platform where best performance may be utilized as a preferred operational goal include: (a) determining which analytically rich aspects, characteristics or features from sensor-observation-derived representations will be utilized to simply or efficiently answer selected questions, (b) determining the selection of points or areas of or from analytically rich aspects, characteristics or features from sensor-observation-derived representations that will be located through utilization of measure points, (c) capturing first or second series sensor observations, (d) processing sensor observations, (e) locating selected measure points on sensor-observation-derived representations, (f) assigning appropriate informational representations regarding or utilizing selected analytically rich aspects, characteristics or features of or from sensor-observation-derived representations, (g) providing structured storage of informational representations regarding or utilizing: (i) sensor observations, (ii) subjects of sensor observations, or (iii) measure points; (h) utilizing measure points that are located on sensor-observation-derived representations, (i) utilizing appropriate informational representations regarding or utilizing sensor-observation-derived representations in the making of selected cyber determinations, (j) standardization of at least one member selected from the group consisting of: (i) processes, (ii) procedures, (iii) selection of processes or procedures to utilize, (iv) processing of sensor observations, (v) storing data, (vi) utilizing data, (vii) selecting of sensor data from sensor observation datasets, (viii) deriving data, (ix) assignment or utilization of definitions, (x) making of measurements, (xi) utilization of units of measure, (xii) making adjustments for differences between first series observations or observation circumstances and second series observations or observation circumstances, or (xiii) making selected cyber determinations; (k) any other aspect of the operations of the platform selected from a spectrum of other aspects of the operations of the platform, or (l) any combination thereof.

The platform is configurable for making selected cyber determinations regarding or utilizing sensor observations or sensor observation subjects by means of matching or comparing informational representations regarding or utilizing yet-to-be-determined analytically rich aspects, characteristics or features of or from second series observations or second series observation subjects with comparable informational representations regarding or utilizing known analytically rich aspects, characteristics or features of or from first series observations or first series observation subjects.

The platform is configurable for achieving a goal of having the same outcome occur every time the same observation is processed as a part of a first series observation or as a part of a second series observation.

The platform utilizes standard processes or standard procedures to best achieve the goal of same outcomes from sensor observations of the same subject under differing sensor observation circumstances. As an example, a first series observation is made of a person under a specific set of observation circumstances, and standard processes or standard procedures are utilized for assigning appropriate standard informational representations regarding or utilizing the sensor observation of the person. When the same person is observed by a different sensor at a different time under a different set of observation circumstances, the platform is configurable for utilizing standard adjusting factors to compensate for the differences in sensor observation circumstances. The platform's use of standard adjusting factors enables it to assign the same standard informational representations to both of the sensor observations of the same person.

Operations of the platform where standard processes or standard procedures are utilized in the making of selected cyber determinations include: (a) determining which analytically rich aspects, characteristics or features of or from sensor-observation-derived representations will be located through utilization of measure points, (b) determining which standard target sets of measure points will be utilized for specific observation subjects or observation circumstances, (c) determining which measure points will be included in each standard target set of measure points, (d) determining the points on sensor-observation-derived representations where selected measure points are to be located, (e) appropriately assigning or utilizing standard informational representations regarding or utilizing analytically rich aspects, characteristics or features of or from sensor observations or sensor observation subjects, (f) determining the sensors that were utilized in the making of sensor observations, (g) determining matches between informational representations from second series observation concise datasets and comparable informational representations from first series observation concise datasets, (h) deriving informational representations from the processing of first series observation informational representations or second series observation informational representations, (i) utilizing informational representations that were derived from the processing of first series observations or second series observations, (j) utilizing standard informational representations or definitions regarding or utilizing any aspects of the operations of the platform, or (k) utilizing standard units of measure or methods of making measurements in the making of measurements regarding or utilizing sensor observations or sensor observation subjects.

The platform is configurable for utilizing non-platform-standard processes or procedures. However, the informational representations regarding or utilizing sensor observations or sensor observation subjects from the non-platform-standard processes or procedures will need to be either an exact match to or be translated or adjusted to match the platform's standard process or procedure assigned informational representations.

The platform is configurable for being persistent in attempting to achieve selected cyber determination goals. As an example, should a selected determination based upon conclusions from comparing informational representations regarding measure points or analytically rich aspects, characteristics or features from a first series observation of one specific person's face not result in the making of a selected cyber determination of identity, then the platform is configurable for continuing comparing or determining operations until the selected determination has been made, or there are no further comparable first series observation concise datasets to compare to available second series observation concise datasets.

The spectrum of sensors that the platform is configurable for utilizing includes: (a) light sensors that sense any spectra of light, (b) odor sensors, (c) temperature sensors, (d) pressure sensors, (e) energy sensors, (f) image sensors that utilize any spectra of light, (g) odor sensors, (h) chemical sensors, or (i) any other types of sensor that may be used in the capturing of sensor observations that are utilizable in the making of selected cyber determinations.

The platform is configurable for interacting with cyber resources that are being utilized by the platform. The interacting is utilized for altering the operations of those resources for any purpose, including for the purpose of capturing any possible sensor observations or providing any useful variations of the operations of utilized cyber resources.

Through the incredible speed and power of cyber resources, any large number of criteria may be collectively or selectively utilized for any aspect of the operations of the platform.

Every aspect of the operations of the platform can be configurable for utilizing selected choices of predetermined criteria. Criteria are selected from a spectrum of criteria that are predetermined: (a) by a person, (b) as an integral part of the operations of the cyber resources that are being utilized by the platform, (c) as a part of the operations of the platform, (d) utilizing any other means for selecting criteria, or (e) any combination thereof. Selection of anything also constitutes selecting criteria.

Criteria are selected choices of who, when, where, what, why or how as each relates to any aspect of the operations of the platform. Providing a choice of any possible criteria and any criteria being possible may well be the most important feature that the family of cyber resources has to offer. The platform is configurable for taking full and best advantage of this particular cyber feature by providing any user with a choice of selection of available criteria regarding any aspects of his or her utilization of the platform.

The platform is configurable for utilizing useful information from any source in the making of selected cyber determinations regarding or utilizing sensor observations or sensor observation subjects. Perhaps the most powerful of all useful information that is utilized by the platform when making selected cyber determinations regarding the identity of any one specific person is information as to exactly who the one specific yet-to-be-identified person is. If the information that the platform utilizes is accurate, then comparison of only one specific person's first series observation concise datasets to the second series observation concise datasets of the one specific yet-to-be-identified person is all that is needed for accurately or reliably making the selected cyber determination regarding the identity of the one specific yet-to-be-identified person.

The platform is configurable for storing data or datasets utilizing any processes or procedures from a spectrum of processes or procedures that are utilized for storing data or datasets that are used in the making of selected cyber determinations.

The platform is configurable for storing informational representations or datasets utilizing storage media from a spectrum of types or variations of storage media that are utilizable for storing informational representations or datasets that are utilized in the making of selected cyber determinations.

The platform is configurable for storing data or datasets for any duration of time selected from a spectrum of durations of time that data or datasets that are utilized in making selected cyber determinations are stored.

The platform is configurable for standardizing any or all aspects of any or all storage operations or storage resources that are utilized by the platform. Standardization of all aspects of all storage operations or storage resources enables storage operations to be performed at the highest attainable percentages of accuracy, reliability, efficiency or simplicity.

The platform is configurable for utilizing data regarding any previous same measurements in the making of selected cyber determinations regarding or utilizing changes in the same measurements that occur over time. Therein lies one of the more powerful features of the platform, selected cyber determinations that are made utilizing changes in measurements or changes in patterns of measurements that occur over time. Measured changes are utilizable in the making of a multitude of selected cyber determinations, many of which are not made or cannot be made by prior art.

Analysis of changes that occur over time is an indispensable part of the accurate or reliable making of a multitude of selected cyber determinations, many of which cannot be made by prior art because much of prior art is not configured or configurable for making selected cyber determinations that utilize informational representations that were derived from, or that utilized changes to same sensor observations or same sensor observation subjects that occur over time.

The platform is configurable for performing structured or unstructured analysis of sensor-observation-derived representations for the purpose of identifying tells that are accurately or reliably utilizable in the making of selected cyber determinations.

Sensor-observable tells that are located through utilization of measure points on sensor-observation-derived representations include: (a) distances or changes in distances between measure points, (b) angles or changes in angles where two or more lines between measure points either cross or meet each other, (c) levels or changes in observed levels of red, green or blue light at one or more pixels at the locations of, or in areas that are located through utilization of measure points, (d) measured pressure or changes in measured pressure at, or in the areas of measure points, (e) measured temperatures or changes in measured temperature at, or in the areas of measure points, or (f) any other measurable changes to analytically rich aspects, characteristics or features that are utilizable as tells, wherein the same measurable sensor-observable tells consistently or reliably are present with the specific events, actions, circumstances or combinations thereof.

The selection of the cyber determinations that are to be made through utilization of one or more specific sensor observations are selected by: (a) people, (b) processes, (c) procedures, or (d) any combination thereof.

Determinations regarding which analytically rich aspects, characteristics or features from sensor-observation-derived representations will be located through utilization of measure points are made by at least one member selected from the group consisting of: (a) people, (b) processes, (c) procedures, or (d) any combinations thereof.

Informational representations regarding or utilizing selected measure points are utilizable by the platform in the making of selected cyber determinations regarding or utilizing at least one member selected from the group consisting of: (a) the locations of selected measure points, (b) a measure point's measured relationship with at least one other measure point, (c) the exact point where a measure points locate analytically rich aspects, characteristics or features from sensor-observation-derived representations, (d) areas of analytically rich aspects, characteristics or features from sensor-observation-derived representations that are located through the utilization of measure points, (e) analytically rich aspects, characteristics or features from sensor-observation-derived representations that are separated by lines between two or more measure points, (f) sensor-observation-derived representations of odors, (g) sensor-observation-derived representations of pressures, (h) sensor-observation-derived representations of temperatures, or (i) any other sensor-observation-derived representations of analytically rich aspects, characteristics or features that are located through utilization of measure points.

The platform is configurable for utilizing the smallest possible number of informational representations regarding the smallest possible number of selected analytically rich aspects, characteristics or features from the smallest possible number of sensor-observation-derived representations as are needed for the making of the smallest possible number of intermediate cyber determinations that are needed for the making of selected final cyber determinations regarding or utilizing sensor observations or sensor observation subjects.

Further, the platform is preferably configured for providing or utilizing concise datasets wherein the informational representations from concise datasets are as analytically rich as needed for utilization in the making of selected cyber determinations, and concise to the point where, if there were any fewer informational representations it would not be possible to accurately or reliably make selected cyber determinations. Additionally, concise datasets are preferably configurable to include few, if any unnecessary informational representations.

The platform is configurable for utilizing informational representations from original sensor observation datasets that range from being the least complex in regard to overall size or complexity, to being extremely complex in regard to the overall size or complexity. An outdoor light sensor observation is an example of a very small and simple set of informational representations from a sensor observation, wherein the platform is configurable for assigning appropriate informational representations regarding the specific times the sensor observation indicated a specific threshold high level of observed light first occurs, and other informational representations are appropriately assigned when the light sensor observation indicates a threshold low level of observed light first occurs.

Video-formatted image sensor observations are an example of very large and complex original sensor observation datasets. As an example, a 1080P video-formatted image sensor is configured for providing a stream of at least thirty sequential two-million pixel images per second. Wherein each of the two-million pixels from each image has standard information regarding the one specific pixel which includes the pixel's specific horizontal line location and vertical line location on the pixel grid, as well as the levels of red, green and blue light that were observed at the pixel.

Compressing very large original sensor observation datasets into concise datasets yields many advantages. These advantages include: (a) concise working datasets; as an example, 1080p video-formatted image sensor observations of a person's face may be compressed down to concise working datasets regarding a standard target set of 17 facial measure points. Wherein the original sensor observation dataset that is comprised of informational representations regarding more than two-million pixels per image is compressed down to a concise dataset that is only comprised of selected sensor data regarding only the 17 selected measure point located pixels per image, (b) reduction of the amount of data that is stored or used in the making of selected cyber determinations, (c) reduction in the amount of data that is processed in the making of selected cyber determinations; it is much more efficient to store, process or use informational representations regarding the 17 pixels at the 17 selected measure points than it is to store, process or use informational representations regarding each of the more than two million pixels that make up the original sensor observation dataset for each sequential video-formatted image, (d) certain cyber determinations cannot be made by prior art, but can be made by the platform through its utilization of informational representations from concise datasets, or (e) any other advantages that the compressing of very large original sensor observation datasets into analytically rich concise datasets enables.

Concise datasets are comprised of selected sensor data or selected derived data.

Selected sensor data are comprised of one or more original informational representations that have been selected from original sensor observation datasets by a person or by processes or procedures of the platform.

Selected sensor data are preferably configurable for being comprised of the smallest possible amount of data that will be needed for the accurate or reliable answering of selected questions regarding or utilizing sensor observations or sensor observation subjects.

When using selected sensor data regarding only 17 pixels from each sequential video image of a person's face, it may seem like this sensor data would be useless in the making of almost any selected cyber determination. However, with analysis over time, the selected sensor data regarding the 17 pixels is analytically rich and through utilization of the platform's extreme analysis processes, procedures or formulas, the platform is configurable for deriving a multitude of data that are indispensable in the making of a multitude of selected cyber determinations.

Extreme analysis is the processing selected sensor data or derived data wherein the processing results in the creation of derived data that are then included in concise datasets. Further, most, if not all derived data are typically derived utilizing the extreme analysis processes or procedures of the platform.

Using one measure point that locates a representation of a pulse point on a sensor-observation-derived representation of a person's face as an example, the following determinations may be made: (a) increases in the observed level of red light at the pixel where the pulse point is located can be used for determining every time a pulse occurs, (b) the number of pulses that occur per minute, (c) the average pulse rate for an hour, day, day, week, during a workout, or when sleeping, (d) using a 23 pixel column or row of pixels that has the measure point at its center, it is possible to determine blood pressure, (e) the average blood pressure for an hour, day, day, week, during a workout, or when sleeping, (f) patterns of changes in pulse rate or blood pressure, (g) changes in patterns of pulse rate or blood pressure over any period of time, or (h) changes in average pulse rate or blood pressure over a week, month, year, or years.

These or any other extreme-analysis-derived informational representations may be included as derived data in the platform's concise datasets where they may be used in real time or at any time thereafter in the making of selected cyber determinations.

Measure points are utilizable for any purpose selected from a spectrum of purposes for which measure points that are utilized in the locating of selected analytically rich aspects, characteristics or features from sensor-observation-derived representations may be utilized.

Determinations regarding which measure points or target sets of measure points will be utilized are made by at least one member selected from the group consisting of: (a) people, (b) processes, (c) procedures, or (d) or combination thereof.

Measure points provide the structure, continuity or common elements that are needed to standardize or unify the different operations of the platform when those operations are performed at different times, or under the same or different observation circumstances. Through use of the standardization or structure that is enabled by utilization of measure points, the platform is configurable for utilizing the same standard processes or procedures in the making of same or similar cyber determinations.

The structure that is provided by utilization of measure points or target sets of measure points enables interoperable use of the disclosed process, procedures or components thereof across multiple types of computing processes, systems or environments. Utilization of measure points provides the structure and common elements that are needed to: (a) standardize, (b) unify, or (c) synchronize, the operations of the different processes or procedures of the disclosed platform whenever or wherever they are performed.

A spectrum of purposes for which measure points may be utilized in the making of selected cyber determinations includes: (a) providing points from which to measure, including measurements of light, temperatures, pressures, colors, odors, chemical signatures, distance, degrees of angles, locations, orientation, time, or any other measurements selected from a spectrum of measurements where measure points may be utilized, (b) locating, on image-sensor-derived representations, the corners or boundaries of selected areas of pixels or scalable configurable grids, (c) locating, from image-sensor-derived representations, differences or patterns of differences between adjoining pixels that indicate edges or other selected analytically rich aspects, characteristics or features, (d) as parts of standard target sets of measure points, (e) identifying measure points from standard target sets of measure points whose corresponding analytically rich aspects, characteristics or features could not be located on sensor-observation-derived representations, (f) locating faces on image-sensor-derived representations, or (g) any other purpose selected from a spectrum of purposes for which measure points that are used in the locating of analytically rich aspects, characteristics or features of or from sensor-observation-derived representations may be utilized.

Measure points may be utilized by the platform in the making of selected measurements, whereby informational representations regarding results of the measurements are stored or utilized by the platform in the making of selected cyber determinations. Examples of measurements regarding or utilizing observed analytically rich aspects, characteristics or features from sensor-observation-derived representations that are useable in the making of selected cyber determinations include: (a) measured odors, (b) measured chemical signatures, (c) measured temperatures, (d) measured pressures, (e) measured colors, (f) measured levels of colored light, (g) measured brightness, (h) measured distances between measure points, (i) measured angles where lines between measure points cross or meet, (j) measured speeds, (k) measured time, or (l) any other measurements regarding or utilizing measure points. In addition, the platform is configurable for utilizing changes to selected measurements that occur over time in the making of selected cyber determinations.

The platform is configurable for determining where to locate measure points on sensor-observation-derived representations where they can best be utilized in the locating of sensor-observable changes or tells that reliably occur over any part of a series of sensor-observation-derived representations. The platform is configurable for utilizing selected tells in the making of selected cyber determinations.

The platform is configurable for utilizing measure points at only the analytically rich aspects, characteristics or features that are needed for the making of selected cyber determinations.

Determinations regarding which analytically rich aspects, characteristics or features of or from sensor-observation-derived representations will be located through utilization of measure points are made by at least one member selected from the group consisting of: (a) people, (b) processes, (c) procedures, or (d) any combinations thereof.

Guiding factors for determining which analytically rich aspects, characteristics or features from sensor-observation-derived representations will be located on sensor-observation-derived representations through utilization of measure points includes: (a) which analytically rich aspects, characteristics or features from sensor-observation-derived representations are needed for the making of selected cyber determinations, (b) which sensor-observable changes that occur over time are needed for the making of selected cyber determinations, (c) which analytically rich aspects, characteristics or features that are locatable through utilization of measure points are present or observable in similar sensor observations or sensor observation subjects, (d) do all or most similar sensor observations or sensor observation subjects have the same or similar analytically rich aspects, characteristics or features to locate through utilization of measure points, (e) are the standard processes or standard procedures of the platform utilizable in the selecting of analytically rich aspects, characteristics or features that will be utilized in the making of selected cyber determinations, or (f) any other factors that influence the selection of which analytically rich aspects, characteristics or features of or from sensor-observation-derived representations will be located on sensor-observation-derived representations through utilization of measure points.

When making selected cyber determinations utilizing video-formatted image sensor observations of a person's face, it is only necessary to utilize two analytically rich features in the making of the selected cyber determination: Is the driver of a vehicle falling asleep? The first analytically rich feature is the bottom center of one of the driver's upper eyelids; the second analytically rich feature is the top center of the lower eyelid of the same eye. Measure points are utilized in the locating of both analytically rich features. Wherein the measured distance between the two measure points is utilized in the making of the selected determination as to whether or not the vehicle driver's eyelids are closed. Should the driver's eyelids be determined to be closed for a specified duration of time or longer, then the platform is configurable for determining that the vehicle's driver is falling asleep or has fallen asleep. Additionally, should the horizontal pixel grid line that each of the two measure points are located on drop a certain distance or more together over a certain duration of time, it is reliably determinable that the person's head has dropped as he or she nodded off to sleep.

It may be quite easy for a person to determine where measure points should be located on sensor-observation-derived representations. As from the previous example, a person's selection of the two specific measure points enabled the operations of the platform to utilize a simple, concise and efficient combination of sensor-observed behaviors that were compressed into a few standard informational representations that are utilizable by the platform in the making of the selected cyber determination as to whether or not the driver of a vehicle is falling asleep or has fallen asleep.

The platform is configurable for selecting and utilizing standard target sets of measure points. Selecting and utilizing standard target sets of measure points is done for: (a) the purpose of including, in standard target sets, only the selected measure points that may be possible to locate on specific sensor-observation-derived representation that are observed under specific observation circumstances; for example, a different standard set of measure points is utilized for a full frontal representation of a person's face than would be utilized for a side view of the same person's face and head, (b) the purpose of including, in standard target sets, only the measure points that are needed in the making of selected cyber determinations; for example, a standard target set of measure points that is used in the locating of the centers of pupils and inside or outside corners of eyes is utilizable in the making of selected cyber determinations regarding the direction, in terms of up, down, left, or right, that a person is looking, (c) the purpose of determining exactly what a person is looking at, (d) the purpose of locating specific occurrences such as selected increments of time that have elapsed, or selected increments of change in temperature that have occurred since the most recent measure point was located on a sensor-observation-derived representation of a temperature sensor observation, (e) the purpose of determining which standard target sets of measure points to utilize in the processing of second series observations that will be compared to specific first series observations wherein, in an effort to achieve a highest attainable percentage of cyber determination accuracy, the same standard target set of measure points that were utilized for a first series observations should be utilized for comparable second series observations, or (f) for any other purpose from a spectrum of purposes for which selecting or utilizing standard target sets of measure points may be done.

The points on sensor-observation-derived representations upon which selected measure points are located can differ substantially under different observation circumstances. It is therefore necessary for the platform to be configurable for utilizing more than one standard target set of measure points for the same observation but under differing observation circumstances, with each different standard target set of measure points being configured to enable the making of selected cyber determinations regarding or utilizing the same or similar sensor observations or sensor observation subjects but under different observation circumstances.

Determinations regarding which measure points will be included in each different standard target set of measure points are made by at least one member selected from the group consisting of: (a) people, (b) processes, (c) procedures, or (d) any combinations thereof.

The platform is configurable for locating every measure point from a standard target set that can be located. Informational representations regarding measure points from standard target sets that the platform was unable to locate may also be stored or utilized in the making of selected cyber determinations.

The platform is preferably configurable for utilizing as few target sets of measure points as can possibly be used in the accurate or reliable making of selected cyber determinations. Wherein each standard target set of measure points preferably includes as few measure points as could possibly be used for accurately or reliably making selected cyber determinations.

Standard target sets of measure points add the structure that is needed to process comparable first series sensor observations and second series sensor observations in the same way.

The platform is configurable for assigning or utilizing standard measurements, standard designations, standard informational representations or standard definitions to represent observations, subjects of observations, measure points, measurements, or any other analytically rich aspect, characteristic or feature of or from the operations of the platform.

The appropriate standard informational representations to assign to analytically rich aspects, characteristics or features are selected by at least one member selected from the group consisting of: (a) people, (b) processes, (c) procedures, or (d) any combination thereof.

Standard informational representations that are assigned or utilized include: (a) standard informational representations identifying the specific sensor observation that informational representations are associated with, (b) standard informational representations identifying the specific time or times that specific sensor observations or parts thereof were captured, (c) standard informational representations regarding the sensors that were utilized in the making of observations, (d) standard informational representations regarding the circumstances of sensor observations, (e) standard informational representations regarding which standard target sets of measure points were used, (f) standard informational representations regarding processes or procedure that were utilized, (g) standard informational representations regarding selected analytically rich aspects, characteristics or features, (h) standard informational representations regarding analytically rich aspects, characteristics or features at the locations of measure points, or in areas that are located through the utilization of measure points, (i) standard informational representations regarding measured location or measured orientation of measure points that are at the exact locations of or in the areas of selected analytically rich aspects, characteristics or features of or from sensor-observation-derived representations, (j) standard informational representations regarding measured location or measured orientation of measure points on sensor-observation-derived representation, or in relation to other analytically rich aspects, characteristics or features that are located by measure points on the same sensor-observation-derived representation, or (k) any other standard informational representations regarding or utilizing any other analytically rich aspects, characteristics or features of or from measure points, sensor observations, sensor observation subjects or sensor-observation-derived representations.

Utilization of one, and only one, standard set of informational representations is an important part of accurately, reliably and consistently making selected cyber determinations of identity. A concise datasets identity test is configurable for making, on a worldwide basis, consistent and accurate assignments of standard informational representations to any analytically rich aspect, characteristic or feature of or from sensor-observation-derived representations of people.

The platform is configurable for utilizing standard adjusting factors to compensate for differences between second series observations and first series observations. These differences include differences in: (a) lighting, (b) pose, (c) location, (d) movement of sensors, (e) movement of subjects of sensor observations, (f) parts of the observation subject that were observed, (g) wind conditions, (h) sensors that were used for observations, or (i) any other differences between second series observations and first series observations that can be compensated for through utilization of the platform's standard adjusting factors.

Typically, the processing of sensor observations is broken down into three areas of operations: (a) making selected initial cyber determinations, (b) making selected intermediate cyber determinations, and (c) making selected final cyber determinations. In some cases, all or any part of what was determined when making initial cyber determinations will result in the making of at least one selected final determination. Further, the making of any one or more intermediate cyber determinations may also result in the making of one or more selected final cyber determinations. In addition, prior intermediate or final cyber determinations may be utilized in the making of subsequent selected intermediate or final cyber determinations wherein the previous cyber determinations may have been made, at least in part, to enable the making of one or more subsequent selected cyber determinations.

The platform is configurable for reporting on or otherwise utilizing the results of one or more initial, intermediate or final cyber determinations.

The platform is configurable for providing the highest attainable percentages of simplicity, efficiency, accuracy or reliability in the making of selected cyber determinations regarding or utilizing sensor observations or sensor observation subjects, in part, by only performing analysis of the specific pixels or areas of pixels that are needed in the making of selected cyber determinations. Therefore, the platform is configurable for not performing analysis of the pixels that are not needed or utilized in the making of selected cyber determinations.

The platform is configurable for making selected cyber determinations that are not possible to make utilizing only the original sensor observation informational representations from the exact points where measure points are located on image sensor-observation derived representations. When it is not possible to make selected cyber determinations utilizing measure points that each locate only one specific pixel from a sensor-observation-derived representation, then the platform is configurable for analyzing selected groups of pixels utilizing processes or procedures selected from a spectrum of processes or procedures that may be utilized by the platform in the selecting, locating or utilizing of groups of pixels.

The platform is configurable for utilizing three general categories of processes or procedures for accurately or reliably locating measure points on sensor-observation-derived representations of sensor observation subjects:

(a) personalized processes or procedures that are configurable for accurately or reliably and exclusively locating selected measure points on sensor-observation-derived representations of only one specific person or only one other specific observation subject, (b) group processes or procedures that are configurable for accurately or reliably locating selected measure points on sensor-observation-derived representations of any person from specific groups of people or any other observation subject from specific groups of other observation subjects, or (c) generalized processes or procedures that are configurable for accurately or reliably locating selected measure points on sensor-observation-derived representations of any selected people or any other selected observation subjects.

The platform is configurable for achieving highest attainable percentages of accuracy goals when making selected cyber determinations through its use of standard processes or standard procedures that have been trained, taught or configured for accurately or reliably locating selected measure points on sensor-observation-derived representations of only one specific person or only one specific other observation subject. Prior art typically will be trained or taught utilizing a number of different observation subjects that are similar, or, are from a group such as people or cats. The platform is configurable for providing or utilizing standard processes or standard procedures that are trained, taught or configured for exclusively locating selected measure points on sensor-observation-derived representations of only one specific person or only one specific other subject of an observation. Utilization of personally trained, taught or configured processes or procedures is a necessary part of making selected cyber determinations regarding or utilizing the one specific person or one specific other observation subject, including cyber determinations regarding identity, at the highest attainable percentages of accuracy or reliability.

The platform is configurable for locating measure points on sensor-observation-derived representations of people, the sensor observation itself, or any other sensor observation subjects at the highest attainable percentages of accuracy through utilization of processes or procedures that are trained, taught or configured to be utilized for accurately or reliably locating selected measure points on sensor-observation-derived representations of only one specific person, one specific observation or one specific observation subject. The personalized processes or procedures of the platform are configurable for brief utilization, wherein the processes or procedures learn, are taught, or are configured for the accurate or reliable locating of selected measure points for a brief period, such as the use of a facial identity test for one-time access to a gym locker.

The platform is also configurable for accurately or reliably locating selected measure points on sensor-observation-derived representations of only one specific person, observation or observation subject over extended periods of time; for example, one specific person can use a properly configured version of the platform that utilizes personalized processes or procedure in the locating of selected measure points on sensor-observation-derived representations of only the one specific person, wherein these measure points are utilizable in the making of selected cyber determinations, including cyber determination of identity tests, regarding the one specific person at the highest attainable percentage of accuracy or reliability.

When locating measure points on video-formatted image sensor observations of a person's face (or any other observation subject), two types of basic operations may be used. The first operation utilizes processes or procedures for determining the exact initial locations to place selected measure points on one or more sensor-observation-derived representations. Then the disclosed platform may be configured for utilizing tracking processes or procedures for predicting or determining the points where selected measure points are to be located on subsequent sequential sensor-observation-derived representations. Should tracking processes be interrupted, then the exact location of measure points may be determined by performing the processes or procedures that initially determined the locations to place selected measure points.

The platform is further configurable for constantly or intermittently utilizing the initial locating processes or procedures for determining the exact points on each sensor-observation-derived representation upon which selected measure points are to be located.

Examples of where measure points may be located on temperature sensor-observation-derived representations include: (a) the temperature when the sensor observation begins, (b) the point in time when the sensor observation begins, (c) any point in time when there is a one degree change from the measured temperature since the time when the most recent measure point was located on the representation, (d) the temperature when the sensor observation ends, (e) the point in time when the temperature sensor observation ends, or (f) any other points on a temperature sensor-observation-derived representation where measure points are utilizable in the making of selected cyber determinations.

When the platform is utilized for temperature sensor observations, the locating of measure points on sensor-observation-derived representation is straightforward; therefore, complex processes or procedures are not needed for consistently locating measure points at 100% accuracy. However, the making of selected cyber determinations that utilize video-formatted image sensor observations of a person's face require utilization of complex combinations of standard processes or standard procedures for accurately or reliably locating or utilizing selected measure points at the highest percentages of accuracy.

Examples of locations where measure points from standard target sets may be located on image-sensor-derived representations of what has been observed by a forward-facing video camera on a vehicle include: (a) perimeters of buildings, (b) perimeters of benches, (c) perimeters of other vehicles, (d) perimeters of people, (e) perimeters of trees or foliage, (f) edges of sidewalks, (g) edges of curbs, (h) edges of pavement, or (i) any other analytically rich aspects, characteristics or features of subjects of sensor observations that may be made by a vehicle's forward-facing video cameras.

The platform may be configured to utilize a windshield-mounted forward-facing 1080p video-formatted image sensor. The platform utilizes changes that occur in same informational representations: (a) from sensor-observation-derived representation to sequential sensor-observation-derived representation, or (b) over any selected period or periods of time, in the making of selected cyber determinations regarding or utilizing: (i) the exact location of the vehicle, (ii) the speed that the vehicle is traveling, (iii) the vehicle's location on a roadway in regard to lanes, traffic, other vehicles, pedestrians, curbs or markings, (iv) where to stop, or (v) any other selected cyber determinations that may be made using windshield-mounted forward-facing 1080p video-formatted image sensor observations.

The platform is configurable for utilizing measure points in the locating of selected incremental changes that occur over time during sensor observations of analytically rich aspects, characteristics or features of or from the physical world such as temperature, pressure, odor, voltage, amperage, sound, viscosity, speed, moisture, chemical signature or any other sensor-observable analytically rich aspect, characteristic or feature from the physical world. Use of concise datasets that only include specific selected incremental changes in sensor-observation-derived measurements will typically result in a best performing blend of an as simple, concise and efficient as possible means of recording or utilizing informational representations regarding or utilizing selected analytically rich aspects, characteristics or features.

The platform is configurable for utilizing summation table analysis (as later disclosed) in conjunction with scalable configurable grids as a part of the processes or procedures that are utilized in the making of selected predictive cyber determinations regarding where to locate selected measure points on subsequent sequential sensor-observation-derived representations. Further, the platform is configurable for utilizing smudge analysis (as later disclosed), darkest pixel analysis, lightest pixel analysis or any other method of analysis selected from a spectrum of methods for predicting or determining where to locate selected measure points on subsequent sequential sensor-observation-derived representations.

Utilization of measure points for accurately or reliably locating selected analytically rich aspects, characteristics or features of or from sensor-observation-derived representations is not the only combination of processes or procedures that the platform is configurable for utilizing in the making of selected cyber determinations. The platform is configurable for making selected cyber determinations through utilization of any processes or procedures selected from a spectrum of processes or procedures the platform may utilize in the making of selected cyber determinations.

At the heart of most cybersecurity failures is the complete inability of computers or cyber resources to constantly and accurately authenticate the claimed identity of any one specific person prior to allowing that person or the cyber devices of that person to first gain initial access and then be allowed to have continued access. Utilizing the platform for accurately and constantly authenticating one specific person's identity as a prerequisite to that person having initial and continued access to cyber resources is an indispensable step in putting an end to cybersecurity failures.

The key to accurately or reliably authenticating any one specific person's identity from cyberspace is the utilization of sensor observations of unique physical, visual, behavioral, physiological or biological aspects, characteristics or features of the person whose identity is being authenticated.

The platform is configurable for making selected cyber determinations regarding the identity of any one specific person (identity tests). These identity tests are utilizable for accurately granting only the one specific known person access to his or her own personal, private or business cyber resources, thereby preventing all others from gaining similar access.

The news of the day when I was writing the first patent application disclosure for this family was about Tim Cook, CEO of Apple Corporation. Mr. Cook talked about how Facebook and many other technology businesses sell collected data about specific people as a product that others use to make any number of cyber determinations regarding any number of aspects or characteristics of the one specific user of Facebook's services. In doing so, Facebook and other technology businesses large and small essentially sell the privacy of their users.

Mr. Cook also spoke of how privacy has been lost and will never come back. I don't think Mr. Cook was right about that! I've been working for many years on a patented collection of cyber architecture, devices, identity tests, processes or procedures that, when properly configured and utilized, will enable every person on the planet to have a very high degree of privacy and security when utilizing any or all cyberspace resources.

The key to enabling a very high degree of privacy and security when utilizing cyberspace resources is to require that any one specific person constantly pass their own identity test prior to being granted initial or continued access to his or her cyberspace resources. Utilizing a concise datasets identity test, any one specific person can configure all or any part of his or her own cyber resources to utilize the identity test for always preventing all others from gaining access.

Cybersecurity failures and the stripping away of each person's personal privacy rights are not the only perils that now plague us from cyberspace. We are also beleaguered by misinformation or disinformation that is delivered throughout cyberspace with malicious intent. Malicious cyber activities include cyber bullying, foreign nations influencing or altering election outcomes, and divisive fictitious materials that are posted on social media to name a few. These threats are each enabled by a malicious actor's complete lack of accountability for his or her activities in cyberspace. The platform as configured for use as an accurate or reliable constantly performed cyberspace identity test is also utilizable for accurately or reliably holding any one specific person accountable for any or all of his or her own cyberspace activities or resources.

One of the greatest concerns of those who are skilled in the art of providing easy to use biologically-based cyberspace identity tests for any one specific person is that the utilized informational representations comprising the cyberspace identity of the one specific person are stolen and then used fraudulently or maliciously. The platform is configurable for constantly making cyberspace identity tests for any one specific person, 4-dimension identity tests that no impostor can pass.

Perhaps the most important single task we will soon utilize computers for will be to constantly provide accurate or reliable cyber determinations regarding any one specific person's identity both prior to and during the entire time that the one specific person is using important cyber resources of any type. The platform, as configured as a constantly performed, 100% accurate cyberspace identity test may be utilized to: (a) put an end to cybersecurity failures, or (b) hold any one specific person accountable for any or all of their cyber resources or their activities in cyberspace.

A technologically interconnected world capable of providing every possible cyber resource humanity could ever want or need can only be built upon the foundation of a secure and safe interconnected cyber environment or cyber ecosystem. Constant utilization of accurate or reliable cyber determinations regarding the identity of any one specific person is an indispensable part of establishing and maintaining a secure and safe cyber environment or cyber ecosystem.

The platform was conceived as a means for providing real time constant testing of any one specific person's claimed identity for the entire period of time he or she is using cyberspace resources. One particular standard target set of seventeen measure points that the platform utilizes in the locating of specific selected analytically rich aspects, characteristics or features from sensor-observation-derived representations of a person's face can constantly be utilized in the accurate or reliable testing of any one specific person's identity.

The platform, is configurable for making 100% accurate cyber determinations regarding the identity of any one specific person utilizing as few or as many unique physical, visual, behavioral, physiological or biological characteristics of a person as are necessary to achieve attainable cyber determination of identity goals. When internal and external sensor observations (which can include visual, biological or physiological sensor observations) of a person are utilized, there are a very large number of possible unique combinations of analytically rich aspects, characteristics or features of any one specific person that can be utilized by a concise datasets identity test in the making of cyber determinations of identity. With every unique physical, visual, behavioral, physiological or biological characteristics of a person that has been sensor observed also exists a means for accurately making selected cyber determinations of identity regarding that one specific person.

Using video-formatted image sensor observation of a person's face as an example, a preferred standard target set of seventeen measure points are accurately or reliably located on each sequential sensor-observation-derived frontal representation of a person's face. One particular selection of locations for 17 facial measure points include corners of eyes, centers of pupils, bottom centers of upper eyelids, top centers of lower eyelids, tip of nose, centers of left and right jawlines, corners of mouth, top center of upper lip, and bottom center of lower lip.

Utilizing concise datasets regarding the X and Y line locations on pixel grids and the observed levels of red, green or blue light for only the seventeen pixels where the selected measure points are located enables the platform to constantly make cyber determinations of identity as well as a multitude of other selected cyber determinations regarding or utilizing the person who is the subject of an identity test sensor observation, many of which have yet to be made by prior art.

Informational representations regarding any one specific first or second series observation subject represent the cyberspace identifiers or the cyberspace identity of the one specific observation subject. These cyberspace identifiers may be used to replace the identifiers that are now used such as social security numbers, birth dates, or driver's license numbers, all of which may be easily stolen or replicated and maliciously used by others.

The platform is configurable for determining the exact identity of any one specific yet-to-be-identified person, even when there is no knowledge of who the one specific yet-to-be-identified person might be other than the informational representations from second series observation concise datasets of the yet-to-be-identified person. As an example, the platform is configurable for determining the identity of one specific yet-to-be-identified person by utilizing selected criteria that call for the most unique combination of a person's sensor-observable analytically rich aspects, characteristics or features to be utilized for searching available databases of first series observation concise datasets of known people. This search can continue until either one specific known person is found who absolutely is the same person as the one specific yet-to-be-identified person, or there are no further first series observation concise datasets of comparable known people to search or compare.

Should a cyber identity determination, after conclusions from comparing all available informational representations regarding known people not result in the making of a selected determination of identity goal, then the platform is configurable for utilizing at least one additional sensor observation of the one specific yet-to-be-identified person to add to the second series observation datasets of the one specific yet-to-be-identified person for use in further comparisons.

Far more selected cyber determinations may be made about a specific person through utilization of concise datasets regarding seventeen facial pixels than can be made by prior art through its utilization of the entire two million pixel-per image datasets from the same sensor observations.

The platform is configurable for making selected cyber determinations utilizing specific available sensor observations. Operations of the platform begin with selection of which cyber determinations are to be made. Examples of cyber selected cyber determinations that could be made utilizing image sensor observations of a person's face include what is: (a) a person's identity, (b) a person's hair color, (c) a person's eye color, (d) a person looking at a computer display screen, (e) a person's facial expression, (f) a person's mental or physical state of health, (g) a person's pulse rate, or (h) a person's blood pressure.

Examples of analytically rich aspects, characteristics or features from sensor-observation-derived-representations of people's faces that may be utilized by the platform include: (a) corners of eyes, (b) centers of pupils, (c) tip of nose, (d) corners of mouth, (e) top center of upper lip, (f) bottom center of lower lip, (g) tip of chin, (h) edges of jawline, (i) top center of eyebrows, (j) outer edges of eyebrows, (k) inner edges of eyebrows, (l) pulse points, (m) scars, (n) marks, or (o) tattoos.

Within a spectrum of cyber determinations regarding or utilizing a person as a subject of sensor observations are a multitude of cyber determinations regarding a person including: (a) identity, (b) hair color, (c) moles, (d) wrinkles in skin, (e) freckles, (f) axis point or geometry at joints, (g) scars, (h) height, (i) eye color, (j) pulse rate, (k) blood pressure, (l) blood sugar level, or (m) any other sensor observable aspects, characteristics or features of a person.

Measurements from sensor-observation-derived representations may be utilized in the making of a multitude of selected cyber determinations. One example is the making of selected cyber determinations that utilize facial observations to determine exactly where a person is looking. To do so only requires the use of four measure points that locate four selected analytically rich features from sensor-derived representations of a person's face. Wherein one measure point is selected to be located at a representation of the center of one pupil and one measure point is selected to be located on a representation of the inner corner of the same eye. These two measure points are utilized to determine if the person is looking to the left, straight ahead or to the right, and also to determine if the person is looking up, straight outward, or looking down. The third measure point is selected to be located on a representation of the tip of the person's nose, and the fourth on a representation of the center of his or her left or right jawline. Distances between the third and fourth measure points are utilized to determine if the head is turned to the left, not turned at all, or turned to the right. Further, the difference between the horizontal line location where the measure point at the tip of the nose is located and horizontal line location where the measure point at the center of the jawline is located are utilized for determining if the head is tilted up, not tilted at all or is tilted down. Utilizing data regarding only the four pixels where the four selected measure points are located, it is possible to determine precisely where a person is looking.

Using rapid eye movement patterns as an example of movement that occurs over a very short period of time, if certain rapid eye movement patterns are a reliable indicator that a person has an imminent intent to do harm, then the concise dataset platform can utilize video sensor observations of a person's eye that were captured at a rate of 500 frames per second for identifying the rapid eye movement patterns that occur when a person has an imminent intent to do harm. On the other end of the over-time spectrum, changes that occur over a seven-year period of time in measurements of the range of a person's facial movements may be used to determine that the person has the early onset of Parkinson's Disease and the platform may do so at the earliest sensor detectable point in time. There are a multitude of cyber determinations regarding or utilizing sensor observations or sensor observation subjects that can only be made through utilization of analysis of changes that occur over time, and the platform is configurable for quickly, efficiently or reliably utilizing measure points or concise dataset in the accurate or reliable making of any or all of those selected cyber determinations.

Should it be found that specific image sensor-observable rapid eye movement patterns are accurate or reliable indicators that a person has an imminent intent to do harm, then image sensors that capture 1080p video-formatted images of a person's eyes at a rate of 500 sequential images each second may be utilized in combination with a properly configured version of the platform and other necessary resources in the locating of a standard target set of only two measure points. One measure point locates the center of a sensor-observation-derived representation of a pupil, and a second measure point locates the sensor-observation-derived representation of the inside or outside corner of the same eye. The platform is configurable for utilizing the horizontal and vertical line locations of the two measure points on the pixel grid for accurately or reliably making the selected cyber determination regarding whether or not one specific person has rapid eye movement patterns that reliably indicate the specific person has an imminent intent to do harm.

Further, the rapid eye movement patterns that might indicate a specific person has an imminent intent to do harm could also be detected using the same 1080p video, but video that is captured at the rate of only 30 or 60 sequential images per second. The platform is configurable for utilizing smudge analysis in conjunction with scalable configurable grids wherein one measure point locates a specific point on sensor-observation-derived representations where the white of an eye and the iris meet. The platform is configurable for performing analysis of patterns of, variations in, or smudges in, observed levels of red, green or blue light from the area of the sensor-observation-derived representation where the measure point is located. Sensor observation data from each pixel within a 23-pixel square that includes the selected measure point at its center may then be utilized in the making of the selected cyber determinations as to whether or not one specific person has an imminent intent to do harm.

The platform is further configurable for utilizing a standard target set of measure points that is comprised of only one measure point for performing the functions of a human fingertip controlled touchless user interface. As an example, a person using a laptop computer that has a video camera located at the top of its image display screen is running a touchless user interface (Tui) configured version of the platform. The laptop computer's camera captures video at a rate of 30 images per second. Tui is configured for recording, to a concise dataset, the horizontal and vertical pixel grid line locations of the pixel at the center of a sensor-observation-derived representation of the tip of an index finger. This is performed for each sequential image at a rate of 30 or more images per second. When the person moves their finger the updated fingertip location from the concise dataset is then utilized, in real time, for updating the cursor's location on the laptop computer's image display screen.

The touchless user interface concise dataset that is derived from each sequential image of the sensor observation of the person's fingertip includes only the X and Y line locations and the measurements of observed levels of red, green or blue light at the one pixel where the measure point is located.

The platform is configurable for enabling a person to utilize a video camera for moving a cursor or making a selection at the location of a cursor and it does so without the need for finger to touchscreen contact. Should a person wish to make a selection at a current cursor location, the person does so by moving his or her finger closer to and then farther away from the camera.

Sensor-observed changes in the measured levels of red, green or blue light at the pixel where the single measure point locates the center of the fingertip are used for determining that the person wishes to make a selection at the cursor location.

Examples of prior art human-to-machine interface devices whose full interface functions may be replicated by the platform's utilization of one or more measure points include: (a) mouse interface devices, (b) trackball interface devices, (c) touch screen interface devices, (d) stylus interface devices, (e) keyboard interface devices, or (f) any other human-to-machine interface devices whose functions may be replicated through the platform's utilization of measure points.

Use of touchless user interface technology is not limited to one fingertip nor is it limited to fingertips. Touchless user interface can also be configured for using any or all fingertips, the tip of a nose, an elbow, the gaze of the eyes or any other sensor-observable analytically rich aspects, characteristics or features of a person that can be used to communicate a person's intention to interact with computers or other cyber resources. Touchless user interface may also be configured for offsetting some or all of a disabled person's disabilities when interacting with cyber resources.

Touchless user interface is configurable for having the highest degree of dataset compression that will ever exist: compression at a ratio of N to one, where N is the total number of pixels from the original video image and one is the working dataset regarding the one single pixel from the point where a measure point locates the center of the tip of a person's finger. Touchless user interface's ratio of dataset compression will be over two million to one when using 1080p formatted video.

The platform is configurable for being utilized as a part of a human-to-machine user interface that works in conjunction with any cyber technological device that requires the use of a human-to-machine user interface.

The foregoing principles are further appreciated with respect to FIG. 1, which illustrates a first particular, non-limiting embodiment of utilization of one configuration of the platform in accordance with the teachings herein. As seen therein, a system 101 is provided which comprises a computer 103 equipped with an image display 105 and a video-formatted image sensor 107. The computer 103 has installed, in a tangible, non-transient memory device associated therewith, a computer program which implements the processes or procedures of a touchless user interface configuration of the platform that is used as a human fingertip-to-computer touchless user interface. Accordingly, the computer 103 utilizes the original sensor observation dataset from the image sensor's observations of the person's fingertip in the locating of one measure point at the pixel from the image sensor-observation-derived representations that is at the center of each sequential sensor-observation-derived representations of the person's fingertip 109. The platform utilizes the X and Y line locations of the pixel as a reference that is used for similarly locating a cursor on the pixel grid of the computer's image display screen. The location of the cursor is updated, from video image to sequential video image, when there is a change in the location of the measure point on the sensor-observation-derived representation's pixel grid. The person makes a selection at the location of the cursor by moving their fingertip closer to, and then farther away from the computer's image sensor. Changes in measurements of observed levels of red, green or blue light at the pixel where the measure point is located enables the platform to determine the person wishes to make a selection where the cursor is located on the computer's image display screen. In the particular application depicted, this technique allows the user's finger to be utilized as an alternative to a mouse or stylus for drawing purposes, although it will be appreciated that the same or similar techniques may be utilized for a wide variety of other purposes.

Touchless user interface's concise, efficient and simple center of a fingertip-located measure point technology is utilizable for accurately authenticating the identity of any one specific person. One example of identity authentication requires a person to sign his or her name in the air in front of a video camera. Many factors are utilized for comparing a specific yet-to-be-identified person's signature to the signature of any one specific known person who the yet-to be identified person claims to be. Analytically rich aspects, characteristics or features that are utilized in the making of the selected cyber determination regarding identity include: (a) the line pattern of the signature, (b) behavioral characteristics of movement including movement toward and away from the image sensor, (c) cadence, (d) speed, or (e) timing. Utilizing XYZ location comparison of second series observation concise datasets of signatures with first series observation concise datasets of signatures enables the making of selected cyber determinations regarding claimed identity at the highest attainable percentages of accuracy or reliability. Utilization of the movement of only one fingertip-located measure point is one method of 100% accurate identity authentication that could completely eliminate payment fraud, and do so utilizing methodology that is as simple, concise and efficient as possible.

The platform is configurable for making selected cyber determinations that have not been made or cannot be made by prior art AI and machine learning processes. Further, the platform is configurable for performing structured or unstructured machine learning processes or procedures and it is configurable for doing so more concisely, efficiently and accurately than prior art machine learning processes or procedures.

The platform is configurable for utilizing at least one process or procedure selected from a spectrum of structured or unstructured machine learning processes or procedures that may be utilized in the making of selected cyber determinations regarding or utilizing sensor observations or sensor observation subjects.

Prior art uses unstructured machine learning processes or procedures for providing computer vision or other cyber services or resources. It is not possible to diagnose and then repair prior art machine learning processes or procedures should any part of their operations fail to perform as intended. The inability to diagnose or repair prior art is an insignificant problem when processing data files to facilitate marketing insight. However, it is very risky to use prior art for mission critical purposes such as determining identity for access control, delivering accurate or reliable health care information or diagnoses, or many of the autonomous operations of vehicles or other devices.

The platform is configurable for operating differently than prior art AI or machine learning processes or procedures while making the same selected cyber determinations. It does so by using structured machine learning processes or procedures that utilize measure points for locating selected analytically rich aspects, characteristics or features of or from sensor-observation-derived representations from concise datasets that are configured or structured for consistently being utilizable in the making of accurate or reliable machine learning cyber determinations under same, similar or differing sensor observation circumstances. Additionally, the structured machine learning processes or procedures of the platform are configurable for being easily diagnosed, repaired or altered should they fail to perform as intended.

The platform is configurable for utilizing structured machine learning process or procedures in the making of selected cyber determinations, wherein measure points that are used in the locating of selected analytically rich aspects, characteristics or features are also utilized by the platform's structured machine learning processes or procedures for establishing or maintaining the structure that is needed for consistently locating, through utilization of measure points, selected analytically rich aspects, characteristics or features from sensor-observation-derived representations. The structured or unstructured machine learning processes or procedures of the platform are configurable for being utilized for operational purposes including: (a) grouping measure points into standard target sets of measure points, (b) determining which analytically rich aspects, characteristics or features of or from sensor-observation-derived representations are to be located through utilization of measure points, (c) locating selected measure points on sensor-observation-derived representations, (d) assigning appropriate informational representations to selected analytically rich aspects, characteristics or features of or from sensor-observation-derived representations, (e) storing selected informational representations in the structured environments of concise datasets, (f) utilizing informational representations from concise datasets in the making of structured or unstructured machine learning cyber determinations, or (g) any other purposes selected from a spectrum of operational purposes that the platform utilizes for performing structured or unstructured machine learning processes or procedures.

The platform is configurable for achieving the highest attainable percentages of simplicity, efficiency, accuracy or reliability through its utilization of selected measure points, standard target sets of measure points, concise datasets or its standard processes or standard procedures in the performing of selected structured or unstructured machine learning processes or procedures.

The platform is configurable for utilizing: (a) unstructured machine learning processes or procedures, (b) structured machine learning processes or procedures, or (c) any combination thereof, in the making of selected cyber determinations regarding or utilizing sensor observations or sensor observation subjects.

In some instances, informational representations regarding selected analytically rich aspects, characteristics or features from sensor-observation-derived representations need to be intermittently or constantly updated with the most recent informational representations regarding: (a) measure points, (b) analytically rich aspects, characteristics or features of or from sensor-observation-derived representations, or (c) analytically rich aspects, characteristics or features from structured machine learning processes or procedures. As an example, a person who has very light-colored eyebrows uses an eyebrow pencil several times a day to give his or her eyebrows a more distinct visual presence. There are slight changes to the observed locations of the eyebrows each time the eyebrow pencil is applied. The platform is configurable for making appropriate changes to selected informational representations regarding the measure points that are utilized in the locating of the person's eyebrows every time the person applies the eyebrow pencil.

The platform is further configurable for utilizing measure points in the making of selected cyber determinations regarding or utilizing the measured location or measured orientation of selected analytically rich aspects, characteristics or features of or from sensor-observation-derived representations of sensor observations or sensor observation subjects.

Examples of cyber determinations regarding the measured location or measured orientation of selected analytically rich aspects, characteristics or features from sensor-observation-derived representations include: (a) measured location or measured orientation of a sensor-observation-derived representation of a scar on a sensor-observation-derived representation of a person's face, (b) measured location or measured orientation of a sensor-observation-derived representation of a mark on a sensor-observation-derived representation of a person's leg, (c) measured location or measured orientation of a sensor-observation-derived representation of a tattoo on a sensor-observation-derived representation of a person's arm, (d) measured location or measured orientation of sensor-observation-derived representations of fingerprint features on a sensor-observation-derived representation of a person's finger or fingerprint, or (e) measured locations or measured orientations of any other selected analytically rich aspects, characteristics or features on sensor-observation-derived representations of sensor observations or sensor observation subjects.

The platform is configurable for providing or utilizing scalable configurable grids in the making of initial cyber determinations, intermediate cyber determinations or final cyber determinations.

Using a video camera observation of a person's face as an example, the platform is configurable for comparing the patterns of measurements of observed levels of red, green or blue light at each of the pixels from within a scalable configurable grid. In this example, a scalable configurable grid is used to define an area of a pixel-based sensor-observation-derived representation where it is anticipated that the measure point that locates the tip of the person's nose will accurately or reliably be located. Patterns of measurements of observed levels of red, green or blue light are analyzed utilizing processes or procedures from a spectrum of processes or procedures that are utilizable in determining where a selected measure points will be located on the pixel grid of a sensor-observation-derived representation.

Scalable configurable grids may be square, rectangular, round, oval or irregularly-shaped.

The platform is configurable for performing structured analysis of all or part of the pixels from within scalable configurable grids.

Two or more pixels are present within each scalable configurable grid.

Scalable configurable grids utilize, scale to, or conform with the pixel grids of sensor-observation-derived representations.

Measure points may be located, for example, at 10, 50 or 100-pixel distances apart on both the X and the Y axes of a pixel grid to form a plurality of groups of pixels from within a scalable configurable grid.

Wherein each group of pixels may be a selected subject of analysis. Wherein results from analysis may be usable in whole or in part in the making of selected cyber determinations. Adjoining or overlapping scalable configurable grid-defined groups of pixels are combinable, wherein combined groups may be utilizable in the making of selected cyber determinations.

Scalable configurable grids are configurable for providing the structure that is needed for performing repeated analysis of the same specific selected areas of pixels from each comparable image-sensor-observation-derived representation that is used in the making of selected cyber determinations.

Additionally, analysis of what was observed from within scalable configurable grids may be performed at increasing or decreasing levels of detail as needed. Similarities or differences between informational representations from differently scaled scalable configurable grids may be utilized in the making of initial cyber determinations, intermediate cyber determinations or final cyber determinations.

The platform is configurable for utilizing any processes or procedures from a spectrum of processes or procedures that may be utilized in the making of selected cyber determinations regarding or utilizing groups of pixels that are located within the structures of scalable configurable grids. The platform is also configurable for using any processes or procedures from a spectrum of processes or procedures that may be utilized in the making of selected cyber determinations regarding or utilizing groups of pixels that are located through utilization of one or more measure points.

Summation table processes or procedures are utilizable in combination with scalable configurable grids in the predicting or the making of selected cyber determinations regarding where measure points should be located on upcoming sequential sensor-observation-derived representations. Summation tables are configurable for utilizing scalable configurable grids as the structure that aids in accurately or reliably locating the same group of pixels on every comparable image sensor observation derived representation. Summation table analysis is configurable for utilizing the sums from any or every column or any or every row of measurements of observed levels of red, green or blue light from within a scalable configurable grid in the making of selected cyber determinations.

The sum of all measured levels of red, blue or green light that were observed from each column or each row may be determined and utilized in the making of selected cyber determinations. Additionally, any combination of sums from columns or rows from within scalable configurable grids are utilizable for any purpose selected from a spectrum of purposes for which sums of measurements of observed levels of red, green or blue light from columns or rows from within scalable configurable grids may be utilized. One such utilization is to locate a specific person's face from video-formatted image sensor-observation-derived representations.

The platform is configurable for utilizing summation table analysis for determining how many pixels that selected aspects, characteristics or features have moved from their locations on the previous sequential sensor-observation-derived representation's pixel grid.

Prior art facial recognition processes dedicate the largest percentage of their processing to finding faces. The platform is configurable for comparing second series observation-derived representations with first series observation summation table analysis of a person's face, wherein the platform utilizes informational representations from first series observation summation table analysis of a person's face in the locating of the person's face from second series observation representations.

Utilizing informational representations from summation table analysis of any one specific known person in the finding of that specific person's face from video-formatted image sensor observation-derived representations will result in significant increases in operational efficiencies over prior art. Further, the same summation table-derived informational representations are useable as an initial cyber test of any one specific person's identity. Should it not be possible to use first series summation table informational representations to find the face of the first series observation subject from second series observation-derived representations then the second series observation subject is unlikely to be the person from the first series observation he or she claims to be.

The platform is configurable for accurately or reliably determining that the center of a measure point will be located one-half of a pixel up and one-third of a pixel to the right on the pixel grid of the next sequential sensor-observation-derived representation. This is determined through the utilization of processes or procedures for performing smudge analysis. The platform is configurable for performing analysis of patterns of smudges from image sensor-observation-derived representations in which analysis of measured levels of red, green or blue light, or any other colors of light selected from a spectrum of colors of light, are utilized for accurately or reliably: (a) indicating the presence of remnants of light that was fully present prior to the exact point in time that the specific image was captured, or (b) utilize light from adjoining areas that has reflected or refracted upon specific pixels or specific areas of pixels. The platform is configurable for utilizing analysis of observed presences of remnants of light, reflected light or refracted light in the making of cyber determinations selected from a spectrum of cyber determinations that may utilize smudge analysis.

When viewing a piece of black electric tape that is affixed to a piece of white paper, one might assume that the color of the pixels at the precise edge where the black tape and the white paper adjoin would be black on the tape side and white on the paper side. However, the sensor that is used to capture the image of the tape and paper does not capture the image that way. Light from the black and light from the white impose on each other where black and white adjoin. The imposing of colored light from one pixel to another is due, at least in part, to the reflective or refractive properties of light. The highest level of the imposition occurs at the edge where the black and the white meet as evidenced by the color values for the black are lightest and the color values for the white are darkest at the point where the two colors meet. If the image sensor and the paper and tape are stationary while the image is being captured, then there will usually be a clean graduation of, or mixing of color where black meets white. Should there be no movement of the sensor or the tape and paper, then analysis of the point where tape and paper adjoin will result in the same graduated change of color from each sequential image. Should there be movement of the image sensor or the tape and paper when the sensor observation is captured, then a smudge or smudges in the graduated colors or elongation of graduated colors are reliably observed. The smudge or smudges may be used for any purpose selected from a spectrum of purposes for which smudges from sensor-observation-derived representations may be utilized. One such utilization would be for predicting the directions and distances of movement of measure points from the current pixel grid to the next sequential pixel grid.

Another utilization of smudge analysis is for determining the distance and the direction of movement that occurs from sensor-observation-derived representation to sequential representation when observed movement between images is less than one pixel in distance. Through utilization of smudge analysis, the amount that any of the colors of observed light from one pixel infringe or impose on differently colored light from adjoining pixels is usable by the platform in the making of selected cyber determinations regarding the distance or direction of movement, in fractions of a pixel, that selected analytically rich aspects, characteristics or features have moved on a pixel grid since the previous sensor-observation-derived representation.

In one scenario, a "known person" owns a laptop computer. An identity test configured version of the platform is an integral resource of the known person's laptop computer.

The concise datasets identity test is utilized, in part, for making determinations of identity that are utilized for exclusively granting only the known person access to further use of his or her laptop computer and its resources. The laptop computer includes a video camera that has adjustable pan, tilt and zoom functions that the concise datasets identity test may operate.

The concise datasets identity test captures and processes sensor observations of a known person, the results of which are stored as the known person's first series observation concise datasets. The first series observation concise datasets of the known person are exclusively made up of informational representations regarding the known person. Informational representations that makes up the known person's first series observation concise datasets are utilizable as the known person's cyberspace identity or identifiers.

A cycle of utilization of the concise datasets identity test is initiated by a yet-to-be-identified person requesting use of the known person's laptop computer.

In the instance of this cycle of the utilization of the concise datasets identity test, the platform utilizes the computer's camera to capture video-formatted images of the yet-to-be-identified person. To provide observations that would be the most likely to aid in making the selected cyber determination of identity, the concise datasets identity test operates the zoom function of the camera to closely frame images of only the face of the yet-to-be-identified person.

As a part of either series of observations, the concise datasets identity test is configurable for locating a standard target set of measure points at specific selected points on image sensor-observation-derived representations of a person's face. The concise datasets identity test is configurable for utilizing the X or Y line locations on the pixel grid or the observed levels of red, green or blue light from each pixel where selected measure points are located in the making of selected cyber determinations.

The concise datasets identity test is further configurable for assigning appropriate informational representations from a standard set of informational representations to selected analytically rich aspects, characteristics or features of or from sensor-observation-derived representations of the yet-to-be-identified person.

Appropriate informational representations that accurately or reliably represent the selected analytically rich aspects, characteristics or features of or from the yet-to-be-identified person's face are assigned and then included in the yet-to-be-identified person's second series observation concise datasets.

In the instance of this cycle of the utilization of the concise datasets identity test, predetermined criteria call for selecting at least one comparable observation concise dataset from the first series observation concise datasets of the person who is the owner of the computer. Further, the at least one selected observation concise dataset is selected because it is the most likely of all available first series observation concise datasets to aid in accurately or reliably making the selected cyber determination as to whether or not the yet-to-be-identified person and the person who is the owner of the computer are the same person.

Wherein the concise datasets identity test utilizes criteria that includes time, date, temperature, light sources, light levels, and the observed portion of the yet-to-be-identified person in the matching of the second series observation concise datasets with at least one comparable first series observation concise dataset of the person who is the owner of the computer.

The platform is configurable for making final determinations regarding many analytically rich aspects, characteristics or features of or from the sensor observations or sensor observation subjects during its assigning of appropriate informational representations. For example, when informational representations were assigned, final determinations were also made that the person who was the subject of the sensor observation had red hair, hazel eyes, a particular geometry and ratio of movement between joints while opening or closing a finger, and many other physical, visual, behavioral, physiological or biological characteristics.

Further, when utilizing an observation with more than one person as a subject, the platform is configurable for excluding from further determinations any person who is a subject of the observation who has been determined to not fit certain parameters. For instance, in keeping with the previous example, the platform is configurable for excluding, from further processing, any person who has been determined to have hair that is not red or eyes that are not hazel. Also, based upon predetermined criteria, one specific yet-to-be-identified person is determined to absolutely not be the same person as the one specific known person if it is determined that the yet-to-be-identified person did not have red hair or hazel eyes.

Wherein matched observation datasets of the yet-to-be-identified person and the person who is the owner of the computer are compared by the concise datasets identity test.

Conclusions from comparing informational representations from concise datasets, along with useful information, are utilized in the making of selected cyber determinations.

In this instance, the concise datasets identity test compares informational representations from second series observation concise datasets to informational representations from first series observation concise datasets wherein both first series and second series observation concise datasets are comprised of informational representations regarding only the pixels where selected measure points are located or pixels in structured areas that are located through utilization of measure points. The concise datasets identity test is configurable for making adjustments, as a part of comparing operations, for differences in observation circumstances or other differences between first series observations and second series observations.

Comparison of second series observation concise datasets to first series observation concise datasets provides an overabundance of physical, visual, behavioral, physiological or biological characteristics that are utilizable in the accurate or reliable making of the selected cyber determination of identity. Far more comparable analytically rich aspects, characteristics or features exist than are needed for making the selected cyber determination, with essentially 100% accuracy, that the yet-to-be-identified person and the person who is the owner of the laptop computer absolutely are the same person.

Once the selected cyber determination has been made, the concise datasets identity test is configurable for reporting the determination.

Wherein the determination that the yet-to-be-identified person and the owner of the laptop computer absolutely are the same person is reported to a history that the concise datasets identity test maintains and also to programming running on the laptop computer. Having received the real-time report from the operations of the concise datasets identity test that the yet-to-be-identified person absolutely is the same person as the owner of the laptop computer, the laptop computer then grants its owner exclusive access to use of its resources. History or any other aspects of the operations of the platform disclosed herein are stored in volatile or non-volatile memory, e.g., in one or more storage modules that are utilized by one or more computers.

In order to best demonstrate a few selected further utilizations of the processes or procedures disclosed herein, it is helpful to consider the future, which is illustrated with reference to Single-Point-of-Access Cyber Systems or Point-of-Cyber-Access Cyber Systems. This is advantageous in that the Single-Point-of-Access Cyber System and the Point-of-Cyber-Access Cyber System enable technologically interconnected cyber environments or cyber ecosystems that are configured to enable the full and the best utilization of the disclosed concise datasets platform.

To begin, the Single-Point-of-Access Cyber System or the Point-of-Cyber-Access Cyber System architectures provide each person with one remotely accessible point of cyber access computer. Each person can utilize any mobile or stationary remote terminal-type of device that is called a cyber portal to gain secure and private access to his or her own remotely located point of cyber access computer.

Each person's own remotely located point of cyber access computer is utilizable by the platform in the making of selected cyber identity determinations of a person at levels of accuracy that are up to and include 100% accuracy. In this example, when 100% accuracy has been achieved, the yet-to-be-identified person will be determined to absolutely be the same person as the proprietary user of the point of cyber access computer. This is a cyber determination which must occur before the previously yet-to-be-identified person is granted access to the personal and private resources of his or her own remotely located point of cyber access computer.

A cycle of utilization of the concise datasets identity test is initiated by a yet-to-be-identified person who utilizes a cyber portal to contact and request access to the personal or private resources of his or her own remotely located point of cyber access computer.

Each person's point of cyber access computer is configured so that only one specific person, the point of cyber access computer's proprietary user, can gain access to its personal or private resources, and only after that person has, with 100% accuracy, been determined to be the proprietary user of that specific point of cyber access computer. In this instance, the point of cyber access computer is further configured to require constant authentication of identity during the entire time that its proprietary user is utilizing its resources. The concise datasets identity test that is utilized by the point of cyber access computer is configurable for constantly making cyber determination regarding the identity of its proprietary user, determinations that are made using the video camera component of any cyber portal that is being utilized.

In one non-limiting embodiment, a cyber portal, utilizing its integral camera, captures observations of a yet-to-be-identified person. The original sensor observation dataset from the yet-to-be-identified person is communicated to a remotely located point of cyber access computer. The point of cyber access computer, utilizing the concise datasets identity test and its processes or procedures that are specifically trained, taught or configured to be used for or by only one specific person, utilizes original informational representations from the video dataset in the making of the selected cyber determinations regarding the identity of the person who is using the remotely located cyber portal.

The concise datasets identity test is configurable for controlling operations of pan, tilt or zoom functions of the video camera of the cyber portal for capturing the optimum second series observations of the yet-to-be-identified person.

The concise datasets identity test is configurable for utilizing measure points in the accurate or reliable locating of specific selected analytically rich aspects, characteristics or features of or from image sensor-observation-derived representations of the yet-to-be-identified person's face. Informational representations regarding the X and Y line locations on sensor-observation-derived representation pixel grids along with measurements of the observed levels of red, green or blue light at the pixels where the selected measure points are located are matched or compared with informational representations from the first series observation concise datasets of the proprietary user of the point of cyber access computer.

The concise datasets identity test is configurable for utilizing standard adjusting factors for accurately or reliably making selected cyber determinations when there are differences in observation circumstances or differences in other circumstances between first series observations and the second series observations they are being compared to.

The concise datasets identity test initially and continuously thereafter determines that the yet-to-be-identified person who is requesting access absolutely is the proprietary user of this one specific point of cyber access computer and the proprietary user is thereby granted initial and ongoing access to the personal and private resources of his or her point of cyber access computer.

In light of the foregoing, the Single-Point-of-Access Cyber System or Point-of-Cyber-Access Cyber System requires a person be accurately determined to be the proprietary user of his or her point of cyber access computer before he or she can gain initial access to its personal or private resources. The Single-Point-of-Access Cyber System or Point-of-Cyber-Access Cyber System preferably requires the person also be constantly determined to be its proprietary user when he or she is using his or her own personal point of cyber access computer.

The concise datasets identity test enabled, secure, safe and private technologically interconnected cyber environment or cyber ecosystem of the Single-Point-of-Access Cyber System or the Point-of-Cyber-Access Cyber System is utilizable for providing the planet with vast new cyber resources. Among those resources will preferably be devices that utilize sensors for regularly or constantly monitoring selected aspects of a person's health.

The point of cyber access computer is fully utilizable through use of a cyber portal that is similar in size and worn similarly to a wristwatch. Although a cyber portal with an image display screen of such a small size can require intermittent use of a larger image display screen, a wristwatch-configured cyber portal can nonetheless provide the greatest all-around utility of any cyber portal configuration, in part because a wristwatch-configured cyber portal that includes one or more health metrics sensors can be utilized to securely and privately monitor and report to one's point of cyber access computer any possible sensor-derived health observations (both internal and external).

A person's own personal point of cyber access computer can then utilize those health observations for providing the person (perhaps through use of his or her wristwatch-configured cyber portal) reports of any health information that the person may want or need to utilize or be made aware of.

Through utilization of the security, safety and privacy that is enabled by the cyber determinations of identity that are made by the concise datasets identity test and the resources of the Single-Point-of-Access Cyber System or the Point-of-Cyber-Access Cyber System, it will be possible to securely and privately provide all or part of a person's own personal and private health information to health care practitioners of choice. Doing so should enable the practitioners to provide the person with the best of all possible health care treatments or outcomes.

It will also be possible for a person to anonymously provide all or part of his or her health records to selected others for use in health-related research.

Utilizing a wristwatch-configured cyber portal/health metrics monitor, each person may enjoy the benefits of secure and private uninterrupted observations of any number of measures of his or her health.

When this continuation-in-part disclosure was written the World was being ravaged by the COVID-19 Pandemic. Beyond loss of life and ill health, the pandemic also resulted in lost jobs, lost revenues, failed businesses and financially devastated lives. Widespread use of a concise datasets COVID-19 monitor or a sensor-observation-derived COVID-19 test would have enabled far better control of the virus's spread and would have done so without many of the unwanted consequence.

The platform is configurable for being utilized as a universal health metrics monitor that can constantly monitor a person's stream of health metrics data for any number of known health metrics or health metrics patterns that are reliable indicators of: (a) the onset of adverse health issues, (b) adverse health issues that are occurring, (c) adverse health issues that have occurred, (d) intermediate stages a person's cycle of an adverse health issues, (e) a person is no longer contagious, or (f) the end of a person's adverse health issues.

The universal health metrics monitor disclosed herein is configurable for being utilized as a continuous real-time 24/7 monitor that reliably detects that a person is infected with COVID-19, preferably before the infected person is contagious. An instantaneous real-time interactive alert from the universal health metrics monitor would enable an infected person to contact health care providers and self-quarantine right away, thereby significantly limiting or stopping the spread of the virus.

The universal health metrics monitor may be further configured to monitor the person's health through the entire cycle of their infection. The universal health metrics monitor may also be configured to make a report that an infected person is no longer contagious. Early knowledge that a person is infected along with knowledge of exactly where a person is in their cycle of infection would be valuable tools in providing the person with the best possible health related treatments and outcome.

Knowing a person is no longer contagious would allow that person to end quarantine and safely go back to his or her usual life. In addition, all those who were not found to be infected with the virus could safely go about their lives with the security of knowing they will be instantaneously alerted should their universal health metrics monitor detect they are infected with COVID-19. Allowing those who are not infected or those who were infected but were no longer contagious to safely go about their regular lives would be far better than the methodologies that have been used to date.

The universal health metrics monitor is configurable for monitoring intermittent or continuous stream of sensor data for changes in health metrics data that only occur with people who are known to be infected with COVID-19. Once these are discovered, the changes (tells) from the streams of health metrics data may then be utilized to interactively alert the person that he or she has a COVID-19 infection. In addition, this same simple methodology can be utilized to provide an infected person with interactive alerts at various stages in the cycle of their COVID-19 infection.

Examples of sensor-observable occurrences that could be reliable indicators that a person is infected with COVID-19 include: (a) patterns of movement from coughing or shivering, (b) changes in body temperature, (c) patterns of changes in body temperature, (d) changes in average blood oxygen levels, (e) changes in patterns of blood oxygen levels, (f) changes in patterns of respiration, (g) changes in patterns of blood oxygenation levels during respiration, (h) changes in average blood oxygenation levels, (i) changes in patterns of blood oxygenation levels, (j) the presence of odors or chemical signatures that are only attributable to COVID-19 infections, (k) facial affect, (l) the sound of respiratory abnormalities, or (m) any combination thereof.

The same processes or procedures that were used for discovering the sensor-observable tells of a COVID-19 infection may also be used by the universal health metrics monitor for discovering sensor-observable tells for any adverse health issue from a spectrum of sensor-observable adverse health issues.

As one non-limiting example of use, data streams from odor or chemical sensors are utilized by the universal health metrics monitor for identifying and then reporting on the observed presence of a specific odor or chemical signature that reliably indicates a person has an abnormal cancer cell count. Use of intermittent or constant monitoring for the earliest sensor-detectable specific odor or chemical signature that reliably indicates an abnormal cancer cell count has occurred may be the key to ending cancer-related illness.

Prior art in the field of healthcare utilizes one-time analysis or testing of a person for making health-related determinations or diagnoses. The universal health metrics monitor introduces and enables the use of intermittent or continuous 24/7 monitoring or recording of a person's health metrics. If knowledge is power, then the knowledge that will be gained by the continuous monitoring or recording a person's health metrics may well be the catalyst for the most powerful healthcare advancement we will see in our very long lifetime. One of the advancements will be the discovery of tells that reliably indicate an adverse health issue has occurred or will soon occur. The tells will be found by determining what all people who had the adverse health issue have in common in regard to changes or changes in patterns in their health metrics data that only occur with a common adverse health issue. As an example, should everyone who has a heart attack or stroke experience changes or patterns of changes in their health metrics three days or three hours prior to the adverse health occurrence, then the universal health metrics monitor can be configured to monitor a person's stream of health metrics for the specific changes or patterns of changes that reliably indicate the person will have a heart attack or stroke and alert the person when the reliable indicators are observed.

Using a previous example, a sensor-detectable odor or chemical signature may soon be used to reliably indicate a person had an abnormal cancer cell count. Some part of the people who have this sensor-observed adverse health issue occur will find that it does not persist and quickly goes away. It is quite possible that there may be commonalities between the members of the group, such as they all had big glasses of fresh orange juice. This discovery could lead to a treatment of prescribing the person drink a big glass of fresh orange juice when they are notified by their health metrics monitor that they have an abnormal cancer cell count. This concept for discovering cures is universally useable for any adverse health issues that have been detected by the universal health metrics monitor and then go away without prescribed intervention.

Another example of power that knowledge from use of the universal health metrics monitor will enable is in the area of maintaining optimum health metrics. At present little is known about optimum health metrics or how to maintain optimum health metrics throughout a person's lifetime. Additionally, very little is known about the effects that having less than optimum health metrics play in our mental or physical health or well-being. The universal health metrics monitor is configurable for helping a person achieve and maintain optimum health metrics for the remainder of their life. Optimum health metrics will be unique to each person and the health metrics monitor disclosed herein is configurable for being utilized as a personalized tool that enables a person to achieve any attainable level of optimal health metrics through activity or management of their intake of food, drink, medication or dietary supplements.

Use of changes or patterns of changes in health metrics that occur over time is a very powerful tool that will enable vast improvements in health care methodologies, however use of changes or patterns of changes are not the only methodologies for detecting selected adverse health issues the universal health metrics monitor may utilize. The universal health metrics monitor is also configurable for making at least one selected sensor-observation-enabled health-related determination using data that was derived at one time (a test). Preferably, this type of determination will be made based upon one or more one-time sensor-observations that reliably indicate the occurrence of a selected adverse health-related issue. As an example, dogs are now used to detect the presence of an abnormal cancer cell count or that a person is infected with COVID-19. The universal health metrics monitor is configurable for utilizing sensor observation data to identify the odor or chemical signature that reliably indicates a person has an abnormal cancer cell count or is infected with COVID-19. In the case of COVID-19, having such a test would enable schools, businesses, public transportation, and events to utilize the universal health metrics monitor's COVID-19 tests to safely resume somewhat normal operations.

The universal health metrics monitor and its one-time tests are universal, therefore, the universal health metrics monitor can be configured to provide one-time tests regarding any sensor-observable aspect, characteristic or feature of a person's health selected from a spectrum of one-time sensor-observable analytically rich aspects, characteristics or features of a person's health. This capability will profoundly change how adverse health issues are diagnosed either remotely or in person.

We live in a technologically interconnected world where vast cyber resources presently exist. Within this technologically interconnected world we utilize cyber resources from a spectrum of available cyber resources. This spectrum of available cyber resources is ever widening and over time our technologically interconnected world appears to be destined to provide every possible cyber resource that humanity could ever want or need. When that time comes, the entire body of cyber resources will include—and will rely heavily upon—a scalable configurable universal full spectrum concise datasets platform (such as the scalable configurable universal full spectrum concise datasets platform disclosed herein) that is configurable for utilizing measure points in the locating of selected analytically rich aspects, characteristics, or features of or from sensor-observation-derived representations in the making of not only the presently needed 100% accurate cyber determinations regarding the identity of any one specific person, but also every other cyber determination regarding or utilizing sensor observations or sensor observation subjects that our world could ever want or need.

Invention is the process of merging the future with the present.

Welcome to the future.

One skilled in the art will appreciate that some of the methodologies disclosed herein may be implemented utilizing one or more software programs. Such software programs may take the form of suitable programming instructions disposed in a tangible, non-transient medium which, when implemented by one or more computer processors, perform part or all of the methodologies described herein.

While the disclosed platform has been defined in terms of its preferred and alternative embodiments, those of ordinary skill in the art will understand that numerous other embodiments and applications of the disclosed platform will become apparent. Such other embodiments and applications shall be included within the scope and meaning of the disclosure as defined by the appended claims. Moreover, it is to be understood that the above description of the present disclosure is illustrative and is not intended to be limiting. It will thus be appreciated that various additions, substitutions and modifications may be made to the above described embodiments without departing from the scope of the present disclosure. Accordingly, the scope of the present disclosure should be construed in reference to the appended claims.

What is claimed is:

1. A scalable configurable universal complete spectrum concise datasets platform of processes, procedures, methods, formulas, programming, sensors and computing devices, wherein said concise datasets platform selects, derives or utilizes data for or from concise datasets;
   wherein, said concise datasets are utilizable in the making of at least one selected cyber determination regarding or utilizing at least one sensor observation or at least one sensor observation subject, said concise datasets platform is comprised of:
   a set of resources that include (a) at least one computing device, (b) at least one sensor, (c) selected necessary programming, (d) selected information, (e) criteria selected from a spectrum of criteria that may be utilized by said platform, and (f) other necessary resources; wherein said at least one utilized computing device includes at least one tangible, non-transient memory device and at least one input device or at least one output device;
   wherein said concise datasets platform utilizes all or part of said set of resources for (i) the selecting or deriving of data that is to be included in at least one concise dataset, or (ii) the making of at least one selected cyber determination regarding or utilizing at least one sensor observation or at least one sensor observation subject;
   wherein said at least one concise dataset is utilizable in the making of said at least one selected cyber determination regarding or utilizing said at least one sensor observation or said at least one sensor observation subject;
   wherein said at least one concise dataset is comprised of selected sensor data or selected derived data;
   wherein said selected sensor data is comprised of at least one informational representation that was selected from at least one sensor observation dataset;

wherein said derived data is comprised of at least one informational representation that was derived from the processing of (i) at least one informational representation that was selected from at least one sensor observation dataset, or (ii) at least one informational representation that was selected from derived data;

wherein processes, procedures, methods or formulas that are utilized in the processing of said derived data are selected from a spectrum of processes, procedures, methods or formulas that are utilized in the deriving of data for or from concise datasets;

wherein data from said selected sensor data or said selected derived data are utilizable by said platform in the making of said selected cyber determinations regarding or utilizing sensor observations or sensor observation subjects;

wherein said concise datasets platform is configurable for utilizing at least one measure point in locating of at least one selected analytically rich aspect, characteristic or feature of or from at least one sensor-observation-derived representation of at least one sensor observation or at least one sensor observation subject;

wherein said at least one measure point is utilizable by said platform in the making of said at least one selected cyber determination regarding or utilizing sensor observations or sensor observation subjects;

wherein said at least one analytically rich aspect, characteristic or feature of or from said at least one sensor-observation-derived representation that is located through utilization of said at least one measure point, and said at least one measure point are each assigned at least one appropriate informational representation;

wherein said at least one analytically rich aspect, characteristic or feature of or from said at least one sensor observation or said at least one sensor observation subject are selected from a spectrum of analytically rich aspects, characteristics or features of or from sensor observations or sensor observation subjects;

wherein said at least one analytically rich aspect, characteristic or feature of or from said at least one measure point is selected from a spectrum of analytically rich aspects, characteristics or features of or from measure points;

wherein said at least one cyber determination is selected from a spectrum of cyber determinations that may be made regarding or utilizing sensor observations, sensor observation subjects or measure points;

wherein said spectrum of cyber determinations that may be made regarding or utilizing sensor observations, sensor observation subjects or measure points includes at least one cyber determination that identifies at least one tell that is utilizable in the accurate or reliable making of at least one selected cyber determination regarding or utilizing sensor observations, sensor observation subjects or measure points;

wherein said at least one tell is from a spectrum of sensor-observable tells regarding or utilizing sensor observations, sensor observation subjects or measure points;

wherein said at least one selected cyber determination is utilizable for at least one purpose selected from a spectrum of purposes for which cyber determinations regarding or utilizing sensor observations, sensor observation subjects or measure points may be utilized;

wherein said concise datasets platform is configurable for making said at least one selected cyber determination in real time, or at one or more times thereafter;

wherein said concise datasets platform is configurable for making at least one member selected from the group consisting of (i) one-time single event cyber determinations regarding or utilizing sensor observations, sensor observation subjects or measure points, (ii) intermittently provided cyber determinations regarding or utilizing sensor observations, sensor observation subjects or measure points, or (iii) constantly provided cyber determinations regarding or utilizing sensor observations, sensor observation subjects or measure points;

wherein said selected information is from a spectrum of information that may be utilized by said concise datasets platform in the making of said selected cyber determinations;

wherein said spectrum of information includes information from at least one sensor observations;

wherein said selected information is from one or more points in time, or from one or more periods of time;

wherein said at least one sensor observation is made by at least one sensor selected from a spectrum of sensors that are utilized in the making of selected cyber determinations regarding or utilizing sensor observations or sensor observation subjects;

wherein said concise datasets platform is configurable and all or part of its resource may be configured for utilization in at least one configuration;

wherein said concise datasets platform is scalable in regard to included or utilized concise datasets platform resources to fall at any one point in a range of from a minimum to a maximum, wherein at the minimum said platform is scaled to include or utilize only the resources that are needed in the making of a least complex selected cyber determination, in regard to included or utilized platform resources, and wherein at the maximum said platform is scaled to include or utilize all platform resources;

wherein said at least one sensor observation or said at least one sensor observation subject are selected from a spectrum of sensor observations or sensor observation subjects; and wherein said concise datasets platform further comprises utilizing, in any sequence, at least one part of at least one operation selected from the group consisting of (a) first series observation operations, wherein said concise datasets platform is configured for utilizing at least one first series sensor observation, wherein at least one first series sensor observation or at least one subject of said at least one first series sensor observation has at least one previously determined analytically rich aspect, characteristic or feature, said concise datasets platform recognizes said at least one previously determined aspect, characteristic or feature, said concise datasets platform assigns at least one appropriate informational representation regarding said at least one recognized aspect, characteristic or feature of or from said at least one sensor observation or said at least one sensor observation subject, said at least one assigned informational representation is utilizable by said concise datasets platform in the making of at least one selected cyber determination regarding or utilizing said at least one sensor observation or said at least one sensor observation subject, said concise datasets platform includes at least one assigned informational representation of or from said at least one first series observation in at least one first series observation concise dataset, (b) second series observation operations, wherein said concise datasets platform is configured for utilizing at least one second series sensor observation, wherein at least one second series sensor observation or at least one subject of said at least one second series observation has at least one selected yet-to-be-determined analytically rich aspect, characteristic or feature, said concise datasets platform recognizes said at least one yet-to-be-determined analytically rich aspect, characteristic or feature, said concise datasets platform assigns at least one appropriate informational representation regarding said at least one yet-to-be-determined analytically rich aspect, characteristic or feature of or from said at least one sensor observation or said at least one sensor observation subject, said at least one assigned informational representation is utilizable by said concise datasets platform in the making of at least one selected cyber determination regarding or utilizing said sensor observations or sensor observation subjects, said concise datasets platform includes at least one assigned informational representation of or from said at least one second series observation in at least one second series observation concise dataset, (c) measure point operations, wherein said concise datasets platform utilizes at least one measure point in the locating of at least one selected analytically rich aspect, characteristic or feature of or from at least one sensor-observation-derived representation of at least one sensor observation or at least one sensor observation subject, wherein said concise datasets platform assigns at least one appropriate informational representation regarding said at least one measure point or said at least one selected analytically rich aspect, characteristic or feature, wherein said at least one informational representation is stored or utilized in the making of at least one selected cyber determination regarding or utilizing at least one sensor observation or at least one sensor observation subject, (d) concise datasets operations, wherein said concise datasets platform selects, derives or utilizes data for or from concise datasets, wherein said concise datasets are comprised of selected sensor data or selected derived data, wherein said selected sensor data is comprised of at least one informational representation that was selected from the informational representations of at least one sensor observation dataset, and wherein said selected derived data is comprised of at least one informational representation that was derived from (i) the processing of at least one selected informational representation from said at least one sensor observation dataset, or (ii) the processing of at least one selected informational representation from said derived data, wherein at least one informational representation that was derived from the processing of said at least one selected sensor observation dataset or from said derived data is utilizable by said concise datasets platform in the making of at least one selected cyber determination regarding or utilizing at least one sensor observation or at least one sensor observation subject, (e) matching operations, wherein said concise datasets platform matches at least one selected informational representation from at least one second series observation with at least one selected comparable informational representation from at least one first series observation concise dataset, (f) comparing operations, wherein said concise datasets platform compares at least one selected informational representation from at least one second series observation concise dataset with at least one selected informational representation from at least one first series observation concise dataset, wherein said platform utilizes the comparison (i) for providing at least one conclusion, or (ii) in the making of at least one selected cyber determination, (g) determining operations, wherein said concise datasets platform utilizes said at least one conclusion from said at least one comparing operation, or said selected information, in the making of said at least one selected cyber determination regarding or utilizing at least one sensor observation or at least one sensor observation subject, and (h) reporting operations, wherein said concise datasets platform makes at least one selected report regarding or utilizing at least one aspect, characteristic or feature of or from the operations of said concise datasets platform.

2. The concise datasets platform of claim 1, wherein said concise datasets platform is further configured for: (a) at least one person, (b) at least one process, (c) at least one procedure, or (d) any combination thereof to be utilized in the selecting of at least one aspect, characteristic or feature of or from at least one operation of said concise datasets platform, wherein said at least one process or said at least one procedure are selected from a spectrum of processes or procedures that are utilized in the selecting of the at least one aspect, characteristic or feature of or from at least one operation of said concise datasets platform.

3. The concise datasets platform of claim 1, wherein said concise datasets platform is further configured to utilize at least one member selected from the group consisting of (a) processes, (b) procedures, (c) data, (d) information, (e) interactions by at least one person, or (f) any combination thereof, in the making of at least one selected determination regarding at least one point where at least one selected measure point will be located on at least one sensor-observation-derived representation, wherein said selected processes, procedures, data, information, interactions by at least one person, or any combination thereof are utilizable in the making of at least one type of cyber determination selected from the group consisting of:

(a) cyber determinations of at least one point where at least one selected measure point will be located on at least one sensor-observation-derived representation of only one specific sensor observation subject, (b) cyber determinations of at least one point where at least one selected measure point will be located on at least one sensor-observation-derived representation of at least one sensor observation subject that is one member of at least one specific group of sensor observations subjects, and (c) cyber determinations of at least one point where at least one selected measure point will be located on at least one sensor-observation-derived representation of at least one sensor observation subject from a spectrum of sensor observation subjects.

4. The concise datasets platform of claim 1, wherein said spectrum of subjects of sensor observations includes at least one person as at least one sensor observation subject;

wherein at least one analytically rich aspect, characteristic or feature of said at least one person includes at least one aspect, characteristic or feature selected from a spectrum of analytically rich aspects, characteristics or features of people who are subjects of sensor observations;

wherein at least one measure point is utilizable in the locating of at least one selected analytically rich aspect, characteristic or feature of or from at least one sensor-observation-derived representation of at least one person;

wherein said at least one measure point is utilizable for at least one purpose selected from a spectrum of purposes for which measure points that are utilized in the locating of selected analytically rich aspects, characteristics or features of or from sensor-observation-derived representations of people may be utilized;

wherein said spectrum of analytically rich aspects, characteristics or features from sensor-observation-derived representations of people includes: (a) scars, (b) marks, (c) tattoos, (d) fingerprint features, (e) axis points at joints, (f) tip of nose, (g) corners of eyes, (h) centers of pupils, (i) corners of mouth, (j) tips of fingers, (k) sweat glands, (l) coughs, (m) tremors, (n) shivers, (o) voice, or (p) any other analytically rich aspects, characteristics or features of or from sensor-observation-derived representations of people.

5. The concise datasets platform of claim 1, wherein said concise datasets platform is further configured for making of at least one selected cyber determination regarding or utilizing said at least one sensor observation or said at least one sensor observation subject, wherein at least one sensor observation is made: (a) at one or more points in time, or (b) over one or more periods of time, and said concise datasets platform includes, in at least one concise dataset, at least one informational representation regarding or utilizing at least one selected analytically rich change that occurs over at least one period of time to at least one sensor-observable aspect, characteristic or feature of or from said at least one sensor observation or said at least one sensor observation subject.

6. The concise datasets platform of claim 5, wherein said at least one sensor observation subject is at least one person, and wherein said at least one analytically rich change that occurs over said at least one period of time is at least one change to at least one sensor observable aspect, characteristic or feature of said at least one person selected from the group consisting of sensor-observable analytically rich changes that occur over time to aspects, characteristics or features of a person's: (a) head, (b) face, (c) mouth, (d) eyes, (e) eyebrows, (f) nose, (g) arms, (h) hands, (i) fingers, (j) legs, (k) feet, (l) neck, (m) torso, (n) skin, (o) heart, (p) stomach, (q) intestines, (r) liver, (s) kidneys, (t) lungs, (u) breath, (v) vascular system, (w) brain, (x) spinal cord, (y) neural system, (z) neural activity, (aa) skeleton, (bb) blood, (cc) odor, (dd) voice, (ee) movement, (ff) tip of nose, (gg) corners of eyes, (hh) centers of pupils, (ii) axis points at joints, or (jj) any other aspects, characteristics or features of a person selected from a spectrum of other aspects, characteristics or features of a person where analytically rich sensor-observable changes could occur over time.

7. The concise datasets platform of claim 1, wherein at least one selected cyber determination includes at least one determination of an indicated measure of probability that exists of one specific yet-to-be-identified person being the same person as one specific known person, wherein said at least one cyber determination ranges from the making of at least one cyber determination that said one specific, yet-to-be-identified person absolutely is not said one specific known person, through the making of at least one cyber determination of any intermediate indicated measure of probability that exists of said one specific, yet-to-be-identified person being said one specific known person, to the making of at least one cyber determination that said one specific yet-to-be-identified person absolutely is said one specific known person.

8. The concise datasets platform of claim 1, wherein said concise datasets platform is further configured for making at least one selected cyber determination that is utilized in the process of accurately or reliably granting or denying at least one person or at least one cyber device access to at least one member selected from the group consisting of: (a) all or part of said concise datasets platform, (b) all or part of at least one resource that is being utilized by said concise datasets platform, or (c) all or part of at least one resource that is utilizing said concise datasets platform.

9. The concise datasets platform of claim 1, wherein said concise datasets platform is further configured for being utilized in an accurate or reliable cyber testing of an identity of at least one specific person, wherein at least one concise datasets platform enabled cyber identity test may be configured to utilize at least one selected level of identity test participation by at least one person who is at least one subject of at least one cyber identity test, and wherein said at least one selected level of participation ranges from said at least one person being observable by at least one sensor but not consciously engaged in said at least one cyber identity test, to said at least one person being an observable and consciously engaged participant in said at least one cyber identity test.

10. The concise datasets platform of claim 9, wherein said cyber identity test is further configured to include repeating operations wherein at least one part of at least one first series observation of one specific known person is selected to be repeated by one specific yet-to-be-identified person, wherein said one specific yet-to-be-identified person performs at least one selected repetition, wherein said concise datasets platform assigns at least one appropriate informational representation regarding or utilizing at least one member selected from the group consisting of: (a) said at least one observation, (b) said at least one repetition, or (c) at least one analytically rich aspect, characteristic or feature of or from said one specific yet-to-be-identified person while said yet-to-be-identified person is performing said repetition, wherein said at least one second series observation concise dataset of said at least one repetition includes at least one informational representation that was appropriately assigned to said repetition by said concise datasets platform, and wherein said at least one second series observation concise dataset from said at least one repetition is utilizable in the making of at least one selected cyber determination regarding or utilizing the identity of said yet-to-be-identified person.

11. The concise datasets platform of claim 1 wherein said concise datasets platform is further configured to be utilized as at least one universal health metrics monitor, wherein said at least one universal health metrics monitor is configured for monitoring or recording at least one selected part of at least one sensor observation of at least one selected analytically rich aspect, characteristic or feature of health of at least one person; said universal health metrics monitor is further configurable for making or reporting on at least one selected cyber determination regarding or utilizing at least one selected sensor-observed analytically rich aspect characteristic or feature of the health of a person;

wherein said at least one cyber determination is selected from a spectrum of health-related cyber determinations that may be made regarding or utilizing health-related analytically rich aspects, characteristics or features of or from sensor-observation-derived-representations of people;

wherein said spectrum of cyber determinations regarding or utilizing health-related analytically rich aspects, characteristics or features of or from sensor-observation-derived-representations of people includes at least one cyber determination that identifies at least one health-related tell regarding or utilizing at least one analytically rich aspect, characteristic, or feature of or from at least one sensor-observation-derived-representations of a person, wherein said at least one health-related tell accurately or reliably indicates, in whole or in part, that a person has, had or will have at least one selected health-related occurrence that the person may, should or does want to utilize or be made aware of;

wherein said at least one tell is from a spectrum of sensor-observable tells regarding or utilizing the health of a people;

wherein said at least one health-related tell is utilizable by said universal health metrics monitor in the making of at least one selected cyber determination regarding or utilizing at least one selected sensor-observed analytically rich aspect characteristic or feature of the health of a person;

wherein said at least one selected cyber determination is utilizable by said universal health metrics monitor in the monitoring of, or reporting on, selected sensor observed analytically rich aspects, characteristics, or features of or from a person's health;

wherein monitoring or recording operations of said universal health metrics monitor may be made: (a) as a one-time single event, (b) intermittently, or (c) constantly;

wherein reporting operations of said universal health metrics monitors are configurable for the making of at least one selected report regarding or utilizing at least one health-related analytically rich aspect, characteristic or feature of or from at least one sensor-observation-derived representation of a person selected from a spectrum reports that may be made regarding or utilizing health-related analytically rich aspect, characteristic or feature of or from sensor-observation-derived representations of people;

wherein said recording is made of all or part of at least one selected sensor observation dataset; wherein at least one person or the universal health metrics monitor selects said all or said part of said at least one selected sensor observation dataset that is to be recorded;

wherein said universal health metrics monitor is configurable for including said selected all or said selected part of said at least one sensor observation dataset as selected sensor data in at least one concise dataset;

wherein said at least one sensor observation is made at one or more points in time or over one or more periods of time;

wherein said any other necessary resources include at least one sensor that is utilizable by said universal health metrics monitor in the capturing of at least one selected sensor observation of at least one selected analytically rich aspect, characteristic or feature of a person's health;

wherein said at least one sensor is selected from a spectrum of sensors that are utilized in the capturing of analytically rich health-related observations of a person;

wherein said spectrum of sensors includes: (i) internal sensors, (ii) external sensors, (iii) wearable sensors, and (iv) sensors that are in the observable proximity of a person who is a subject of a sensor's observation.

12. The concise datasets platform of claim 11 wherein said universal health metrics monitor is configurable for being utilized in the making of one or more selected one-time single event health-related cyber test determinations regarding or utilizing at least one selected sensor-observed analytically rich aspect, characteristic or feature of the health of a person;

wherein said selected one or more one-time single event health-related cyber test determinations may be made or utilized in real time or at one or more times thereafter;

wherein said selected one or more one-time single event health-related cyber test determinations are made utilizing at least one sensor selected from a spectrum of sensors that are utilized in the making of one-time single event health-related cyber test determinations regarding or utilizing selected sensor-observable analytically rich aspects, characteristics or features of the health of a person;

wherein said at least one selected analytically rich aspect, characteristic or feature of the health of a tested person is from a spectrum of sensor-observable analytically rich aspects, characteristics or features of the health of people;

wherein the spectrum of health-related cyber test determinations regarding or utilizing selected sensor-observable analytically rich aspects, characteristics or features of the health of a person includes test determinations regarding the presence of: (a) COVID-19, (b) H1N1, (c) Ebola, (d) cancer, or (e) aspects, characteristics or features of a person's health that can be sensor-observed, tested and reported upon;

wherein said one-time single event health-related cyber test determinations regarding or utilizing at least one selected sensor-observed analytically rich aspect, characteristic or feature of the health of a person may be utilized for at least one purpose selected from a spectrum of purposes for which one-time health-related cyber test determinations regarding or utilizing sensor-observed analytically rich aspects, characteristics or features of the health of people may be utilized;

wherein said spectrum of purposes for which one-time health-related cyber test determinations regarding or utilizing sensor-observed analytically rich aspects, characteristics or features of the health of people may be utilized includes the purpose of making at least one health-related cyber test determination regarding or utilizing at least one selected sensor-observed analytically rich aspect, characteristic or feature of the health of any one specific person prior to or immediately prior to the tested person being granted or denied access to at least one member selected from the group consisting of: (i) schools, (ii) public transportation, (iii) houses of worship, (iv) workplaces, (v) events, (vi) sporting activities, (vii) restaurants, (viii) bars, (ix) stores, (x) hospitals, (xi) parks, (xii) prisons, (xiii) nursing homes, (xiv) grocery stores, (xv) theaters, (xvi) gyms, (xvii) health care providers offices, (xviii) concerts, (xix) salons, (xx) meat processing plants, or (xxi) any other places or activities where it may be required or desired to determine if one specific tested person does or does not have at least one selected health-related aspect, characteristic or feature that would or should exclude the specific tested person from gaining initial access or from having continued access to said places or activities.

13. The concise datasets platform of claim 1, wherein said concise datasets platform is further configured to utilize at least one measure point in the locating of at least one sensor-observation-derived representation of at least one selected analytically rich aspect, characteristic or feature of or from at least one sensor-observation-derived representation of at least one face of at least one person;
  wherein said at least one measure point is utilized for at least one purpose selected from a spectrum of purposes for which measure points that are utilized in the locating of analytically rich aspects, characteristics or features of or from sensor-observation-derived representations of faces of people may be utilized;
  wherein said spectrum of purposes for which measure points that are used in the locating of selected analytically rich aspects, characteristics or features of or from sensor-observation-derived representations of faces of people may be utilized includes utilizing at least one measure point for: (a) determining an identity of a yet-to-be-identified person, (b) authenticating the claimed identity of a yet-to-be-identified person, (c) determining a person's facial affect, (d) determining a person's facial expression, (e) determining a gaze of a person's eye or eyes, (f) determining sensor or camera angle, (g) determining sensor observation lighting circumstances, (h) determining a person's pose, (i) determining a portion of a person's face that is being observed, (j) determining at least one measure of a person's state of the mental or physical health, (k) determining a person's pulse rate, (l) determining a person's blood pressure, (m) determining at least one relationship between at least one sensor and at least one measure point that is located on at least one sensor-observation-derived representation of a person's face, or (n) for any other purpose selected from a spectrum of other purposes for which measure points that are used in the locating of selected analytically rich aspects, characteristics or features of or from sensor-observation-derived representations of people's faces may be utilized.

14. The concise datasets platform of claim 1 wherein said concise datasets platform is further configured for the making of at least one selected cyber determination regarding or utilizing at least one measured location of, or at least one measured orientation of, at least one selected analytically rich aspect, characteristic or feature of or from at least one sensor-observation-derived representation of at least one person;
  wherein said at least one sensor-observation-derived representation of said at least one analytically rich aspect, characteristic or feature of said at least one person is selected from a spectrum of sensor-observation-derived representations of analytically rich aspects, characteristics or features of or from people who are subjects of sensor observations;
  wherein at least one measured location of, or at least one measured orientation of said at least one selected analytically rich aspect, characteristic or feature of or from said at least one sensor observation derived representation of said at least one person includes the measured location of, or the measured orientation of: (a) at least one sensor-observation-derived representation of at least one fingerprint feature on at least one sensor-observation-derived representation of a finger or a fingerprint of a person, (b) at least one sensor-observation-derived representation of at least one tattoo on at least one sensor-observation-derived representation of a person, (c) at least one sensor-observation-derived representation at least one scar on at least one sensor-observation-derived representation of a person, (d) at least one sensor-observation-derived representation of at least one mark on at least one sensor-observation-derived representation of a person, (e) at least one sensor-observation-derived representation of at least one sweat gland on at least one sensor-observation-derived representation of a person, (f) at least one sensor-observation-derived representation of at least one pulse point on at least one sensor-observation-derived representation of a person, or (g) any other sensor-observation-derived representations of analytically rich aspects, characteristics or features of a person selected from a spectrum of sensor-observation-derived representations of analytically rich aspects, characteristics or features of people.

15. The concise datasets platform of claim 1, wherein said concise datasets platform is further configured for utilizing at least one measure point in the locating of at least one sensor-observation-derived representation of a tip of at least one finger of at least one person;
  wherein said at least one measure point is utilized for at least one purpose selected from a spectrum of purposes for which measure points that are utilized in the locating of sensor-observation-derived representations of people's fingertips may be utilized;
  wherein said spectrum of purposes for which measure points that are utilized in the locating of sensor-observation-derived representations of people's finger tips includes utilization of said measure points as at least one component of at least one fingertip-to-cyber device touchless user interface; and
  wherein said cyber device is at least one type of cyber device selected from a spectrum of types of cyber devices that may utilize at least one fingertip-to-cyber device touchless user interface.

16. The concise datasets platform of claim 1, wherein said concise datasets platform is further configured to use at least one measure point in the locating of at least one selected analytically rich aspect, characteristic or feature from at least one sensor-observation-derived representation of at least one person for utilization as at least one component of at least one human-to-cyber device touchless user interface;
  wherein said at least one human-to-cyber device touchless user interface, using said at least one measure point, is utilized for at least one purpose selected from a spectrum of purposes for which human-to-cyber device touchless user interfaces may be utilized; and
  wherein said cyber device is at least one type of cyber device selected from a spectrum of types of cyber devices that may utilize at least one human-to-cyber device touchless user interface.

17. The concise datasets platform of claim 1, wherein said concise datasets platform is further configured for utilizing at least one measure point in the locating of at least one axis point from at least one sensor-observation-derived representation of at least one joint of at least one person;
  wherein said at least one measure point that locates said at least one axis point is utilized for at least one purpose selected from a spectrum of purposes for which measure points that locate sensor-observation-derived representations of axis points of joints of people may be utilized; and wherein said spectrum of purposes for which measure points that are utilized in the locating of sensor-observation-derived representations of axis points of joints of people may be utilized includes: (a) the making of at least one selected cyber determination regarding or utilizing a geometry of said at least one sensor-observation-derived representation of said at least one joint, or (b) the making of at least one selected cyber determination that utilizes said at least one measure point in the locating of said at least one axis point on said at least one sensor-observation-derived representation of said at least one joint of said at least one person for at least one purpose selected from a spectrum of other purposes for which measure points that locate axis points of joints from sensor-observation-derived representations of people may be utilized.

18. The concise datasets platform of claim 1, wherein said concise datasets platform is further configured to be utilized in the making of at least one selected cyber determination regarding or utilizing at least one analytically rich aspect, characteristic or feature of the geometry of at least one sensor-observation-derived representation of at least one joint of at least one person; and
wherein said at least one selected analytically rich aspect, characteristic or feature of a geometry of said at least one sensor-observation-derived representation of at least one joint of at least one person is utilized for at least one purpose selected from a spectrum of purposes for which analytically rich aspects, characteristics or features of the geometry of sensor-observation-derived representations of joints of people may be utilized.

19. The concise datasets platform of claim 1, wherein said concise datasets platform utilizes at least one selected measure point in the making of at least one selected measurement;
wherein the at least one measurement that is made through utilization of at least one measure point is selected from a spectrum of measurements that may be made through use of measure points that are utilized in the locating of selected analytically rich aspects, characteristics or features of or from sensor-observation-derived representations; and
wherein said spectrum of measurements that may be made through utilization of said at least one measure point include: (a) measured distances between two or more measure points, (b) measured angles where two or more lines between measure points meet or intersect, (c) measured location of at least one measure point, aspect, characteristic or feature, (d) measured orientation of at least one measure point, aspect, characteristic or feature, (e) measured relationships between two or more measure points, aspects, characteristics or features, (f) time of capture of a sensor observation, (g) measured pressure at, or in an area of one or more measure points, (h) measured temperature at, or in the area of one or more measure points, (i) measured observed level of colored light at, or in the area of one or more measure points, (j) measured grey scale level at, or in the area of one or more measure points, (k) measured odor at, or in the area of one or more measure points, (l) measured presence at, or in the area of one or more measure points, (m) measured sound at, or in the area of one or more measure points, (n) measured energy at, or in the area of one or more measure points, (o) measured chemical presence at, or in the area of one or more measure points, or (p) measures of any other measurable sensor-observable analytically rich aspects, characteristics or features of or from sensor-observation-derived representations that may be located through utilization of measure points.

20. The concise datasets platform of claim 1, wherein any operations of said concise datasets platform or any part thereof may be performed in any useable order or sequence.

21. The concise datasets platform of claim 1, wherein said concise datasets platform is further configured to achieve at least one selected attainable level of accuracy goal for at least one selected cyber determination, and said at least one attainable level of accuracy goal falls in a range extending from 0% accuracy up to, and including, 100% accuracy.

22. The concise datasets platform of claim 1, wherein said concise datasets platform is further configured for utilizing information or informational representations from at least one source that is not at least one first series observation, or at least one second series observation.

23. The concise datasets platform of claim 1, wherein said concise datasets platform is further configured for manipulating the operations of concise datasets platform utilized resources, or any part of the concise datasets platform itself, wherein the manipulating provides said concise datasets platform with selections of possible utilizations, wherein said manipulating is utilized for at least one purpose selected from a spectrum of purposes for which said manipulating can be utilized, wherein said spectrum of purposes for said manipulating includes the purpose of aiding in the making of at least one selected cyber determination.

24. The concise datasets platform of claim 1, wherein at least one part of at least one sensor observation dataset from at least one source that is not at least one first series observation operation is included as at least one part of at least one first series observation dataset, or wherein at least one part of at least one observation dataset from at least one source other than at least one second series observation operation is included as at least one part of at least one second series observation concise dataset.

25. The concise datasets platform of claim 1, wherein said concise datasets platform is further configured to include concise datasets platform history, wherein said concise datasets platform history is comprised of at least one concise datasets platform history record.

26. A concise datasets platform that is comprised of computing devices, sensors, cyber processes and cyber procedures that are utilized for capturing, selecting, deriving or utilizing of data for or from concise datasets, wherein said data for or from said concise datasets is utilizable in the making of at least one selected cyber determination regarding or utilizing at least one sensor observation or at least one sensor observation subject, said concise datasets platform is further comprised of: deriving or utilizing information from at least one point in time or from at least one period of time from a spectrum of information that includes at least one observed aspect, characteristic or feature of or from at least one sensor observation or at least one subject of at least one sensor observation, thereby obtaining sensor-derived information;
wherein said at least one sensor observation is a type of sensor observation selected from the group consisting of (a) visual sensor observations, (b) audible sensor observations, (c) thermal sensor observations, (d) olfactory sensor observations, (e) tactile sensor observations, (f) chemical sensor observations, or (g) any other types of sensor observations selected from a spectrum of other types of sensor observations that may be utilized by said concise datasets platform;

wherein said concise datasets platform captures, selects, derives or utilizes data for or from concise datasets, or makes at least one selected cyber determination through the utilization of (a) at least one computing device, (b) at least one sensor, (c) necessary programming, (d) said information, (e) criteria that are utilized by said concise datasets platform, and (f) any other necessary resources;

wherein said concise datasets platform makes at least one selected cyber determination type from the group consisting of (i) one-time single event cyber determinations, (ii) intermittently made cyber determinations, or (iii) constantly made cyber determinations;

wherein said at least one selected cyber determination is utilized for at least one purpose; and wherein said concise datasets platform further comprises utilizing at least one part of at least one operation selected from the group consisting of (a) first series observation operations wherein said concise datasets platform utilizes at least one sensor observation, wherein said at least one sensor observation or at least one subject of said at least one sensor observation has at least one selected previously determined aspect, characteristic or feature, said concise datasets platform recognizes said at least one selected aspect, characteristic or feature, the at least one selected recognized aspect, characteristic or feature is utilizable by said concise datasets platform in the making of at least one selected cyber determination, said concise datasets platform assigns appropriate informational representations regarding at least one selected known aspect, characteristic or feature of said at least one sensor observation or said at least one sensor observation subject, said concise datasets platform includes at least one of said informational representations in at least one first series observation concise dataset, (b) second series observation operations wherein said concise datasets platform utilizes at least one sensor observation, and wherein said at least one sensor observation or at least one subject of said at least one sensor observation has at least one selected yet-to-be-determined aspect, characteristic or feature, said concise datasets platform recognizes said at least one selected yet-to-be-determined aspect, characteristic or feature, said concise datasets platform assigns appropriate informational representations regarding said at least one selected yet-to-be-determined aspect, characteristic or feature of said at least one sensor observation or said at least one sensor observation subject, wherein said concise datasets platform includes at least one of said informational representations in at least one second series observation concise dataset, (c) measure point operations, wherein said concise datasets platform utilizes at least one measure point in the locating of at least one selected analytically rich aspect, characteristic or feature of or from at least one sensor-observation-derived representation of at least one sensor observation or at least one sensor observation subject, wherein said concise datasets platform assigns at least one appropriate informational representation regarding said at least one measure point, aspect, characteristic or feature of or from said at least one sensor-observation-derived representation, wherein said at least one informational representation is stored or utilized in the making of at least one selected cyber determination regarding or utilizing said at least one sensor observation or said at least one sensor observation subject, (d) concise datasets operations, wherein said concise datasets platform utilizes at least one concise dataset in the making of at least one selected cyber determination, said at least one concise dataset includes selected sensor data or selected derived data, wherein said selected sensor data is comprised of at least one informational representation that was selected from the informational representations of at least one sensor observation dataset, and wherein said selected derived data is comprised of at least one informational representation that was derived from (i) the processing of at least one selected informational representation from at least one sensor observation dataset, or (ii) the processing of at least one selected informational representation from derived data, wherein at least one informational representation from said selected sensor data or at least one informational representation from said selected derived data is utilizable by said concise datasets platform in the making of at least one selected cyber determination regarding or utilizing at least one sensor observation or at least one sensor observation subject, and wherein said selected derived data is derived utilizing at least one method or formula selected from a spectrum of methods or formulas that may be utilized in the deriving of informational representations from sensor data or derived data, (e) matching operations, wherein said concise datasets platform's matching operations include matching at least one informational representation from at least one second series observation concise dataset with at least one comparable informational representation from at least one first series observation concise dataset, (f) comparing operations, wherein said comparing operations include said concise datasets platform's comparing of informational representation from at least one second series observation concise dataset with comparable informational representation from at least one first series observation concise dataset, and providing at least one conclusion or determination from the comparison, (g) determining operations, wherein said concise datasets platform utilizes at least one conclusion or determination from at least one comparing operation or information in the making of said at least one selected cyber determination, and reporting operations, wherein said concise datasets platform's operations include the making of at least one selected report regarding or utilizing at least one aspect, characteristic or feature of at least one part of at least one cycle of utilization of said concise datasets platform.

* * * * *